US006929940B1

(12) United States Patent
Richards et al.

(10) Patent No.: US 6,929,940 B1
(45) Date of Patent: Aug. 16, 2005

(54) **POLYNUCLEOTIDES ENCODING OXALATE DECARBOXYLASE FROM *ASPERGILLUS NIGER* AND METHODS OF USE**

(75) Inventors: Nigel Gordon John Richards, Gainesville, FL (US); Christopher Harry Chang, Gainesville, FL (US); Ammon B. Peck, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/644,123

(22) Filed: Aug. 20, 2003

Related U.S. Application Data
(60) Provisional application No. 60/404,892, filed on Aug. 20, 2002.

(51) Int. Cl.[7] .......................... C12N 9/88; C12N 9/00; C12N 1/20; C12N 1/16; C07H 21/04
(52) U.S. Cl. .................... 435/232; 435/183; 435/252.3; 435/252.33; 435/252.5; 435/256.1; 536/23.1; 536/23.2
(58) Field of Search ................................ 435/183, 232, 435/252.3, 252.33, 252.5, 256.1; 536/23.1, 23.2

(56) References Cited

U.S. PATENT DOCUMENTS

| 5,643,758 A | * | 7/1997 | Guan et al. ................ 435/69.7 |
| 6,297,425 B1 | | 10/2001 | Scelonge et al. |
| 6,355,242 B1 | | 3/2002 | Allison et al. |

FOREIGN PATENT DOCUMENTS

| WO | WO 9842827 | * 10/1998 |
| WO | WO 98/52586 | 11/1998 |

OTHER PUBLICATIONS

Tanner et al. J Biol Chem. Nov. 23, 2001;276(47):43627–34. Epub Aug. 23, 2001.*
Wipat et al. Microbiology. Jun. 1988;144 ( Pt 6):1593–600.*
Wipat et al. Accession AJ223978. Jul. 5, 1999.*
Sanderson et al. Methods Enzymol. 1991;204:248–64.*
Allison, M.J. et al. "Oxalate Degradation by Microbes of the Large Bowel of Herbivores: The Effect of Dietary Oxalate", *Science*, 1981, pp. 675–676, vol. 212, No. 4495.
Allison, M.J. et al. "Oxalobacter Formigenes gen. nov., sp. nov.: Oxalate–Degrading Anaerobes that Inhabit the Gastrointestinal Tract", *Arch Microbiol.*, 1985, pp. 1–7, vol. 141.
Allison, M.J. et al. "Oxalate Degradation by Gastrointestinal Bacteria from Humans", *J. Nutr.*, 1986, pp. 455–460, vol. 116.
Altschul, S.F. et al. "Gapped BLAST and PSI–BLAST: A New Generation Of Protein Database Search Programs", *Nucl. Acids Res.*, 1997, pp. 3389–3402, vol. 25, No. 17.

Anand, R. et al. "Structure of Oxalate Decarboxylate from Bacillus subtilis at 1.75 A Resolution", *Biochemistry*, 2002, pp. 7659–7669, vol. 41.
Baldwin, J. et al. "Mechanism of Rapid Electron Transfer During Oxygen Activation in the R2 Subunit of *Escherichia coli* Ribonucleotide Reductase. 1. Evidence for a Transient Tryptophan Radical", *J. Am. Chem. Soc.*, 2000, pp. 12195–12206, vol. 122.
Bar, G. et al. "High–Frequency (140–GHz) Time Domain EPR and ENDOR Spectroscopy: The Tyrosyl Radical–Di-iron Cofactor in Ribonucleotide Reductase from Yeast", *J. Am. Chem. Soc.*, 2001, pp. 3569–3576, vol. 123.
Basosi, R. et al. "Multifrequency ESR of Copper Biophysical Applications", *EMR of Paramagnetic Molecules*, 1993, pp. 103–150, vol .13, Plenum Press, New York.
Daniel, S.L. et al. "Microbial Degradation of Oxalate in the Gastrointestinal Tracts of Rats", *Appl. Environ. Microbiol.*, 1987, pp. 1793–1797, vol. 53, No. 8.
Dawson, K.A., et al. "Isolation and Some Characteristics of Anaerobic Oxalate–Degrading Bacteria from the Rumen", *Appl. Environ. Microbiol.*, 1980, pp. 833–839, vol. 40, No. 4.
Doane, L.T. et al. "Microbial Oxalate Degradation: Effects on Oxalate and Calcium Balance in Humans", *Nutr. Res.*, 1989, pp. 957–964, vol. 9.
Dunwell, J.M. et al. "Microbial Relatives of the Seed Storage Proteins of Higher Plants: Conservation of Structure and Diversification of Function During Evolution of the Cupin Superfamily", *Microbiol. Mol. Biol. Rev.*, 2000, pp. 153–179, vol. 64, No. 1.
Dutton, M.V. et al. "Oxalate Production by Fungi: Its Role In Pathogenicity and Ecology in the Soil Environment", *Can. J. Microbiol.*, 1996, pp. 881–895, vol. 42, Canada.
Emiliani, E. et al. "Enzymatic Oxalate Decarboxylation in *Aspergillus niger*", *Arch. Biochem. Biophys.*, 1964, pp. 488–493, vol. 105.
Emiliani, E. et al. "Enzymatic Oxalate Decarboxylation in *Aspergillus niger*: Hydrogen Peroxide Formation and Other Characteristics of the Oxalate Decarboxylase", *Biochmica Biophysica Acta*, 1968, pp. 414–421, vol. 167.
Gane, P.J. et al. "Modeling Based on the Structure of Vicilins Predicts a Histidine Cluster in the Active Site of Oxalate Oxidase", *J. Mol. Evol.*, 1998, pp. 488–493, vol. 46.

(Continued)

*Primary Examiner*—Manjunath N. Rao
*Assistant Examiner*—Christian L Fronda
(74) *Attorney, Agent, or Firm*—Saliwanchik, Lloyd & Saliwanchik

(57) ABSTRACT

The subject invention pertains to polynucleotides encoding the enzyme oxalate decarboxylase from the filamentous fungus *Aspergillus niger* and methods of use. The subject invention also pertains to methods of using the enzyme oxalate decarboxylase from *Bacillus subtilis*.

10 Claims, 7 Drawing Sheets

OTHER PUBLICATIONS

Halcrow, M. A. "Chemically Modified Amino Acids in Copper Proteins that Bind or Activate Dioxygen", *Angew. Chem. Int. Ed.,* 2001, pp. 346–349, vol. 40, No. 2.

Halliwell, B. "Non–Enzymic Catalysis of Oxalate Decarboxylate by Light and Flavins", *Biochem. J.,* 1972, pp. 497–498, vol. 129.

Kathiara, M. et al. "Detection and Partial Characterization of Oxalate Decarboxylase from *Agaricus bisporus*", *Mycol. Res.,* 2000, pp. 345–350, vol. 104, No. 3.

Kesarwani, M. et al. "Oxalate Decarboxylase from *Collybia velutips*: Molecular Cloning and its Overexpression to Confer Resistance to Fungal Infection in Transgenic Tobacco and Tomato",*J. Biol. Chem.,* 2000, pp. 7230–7238, vol. 275, No. 10.

Kimmerling, E.A. et al. "Invasive *Aspergillus niger* with Fatal Pulmonary Oxalosis in Chronic Obstructive Pulmonary Disease", *Chest,* 1992, pp. 870–872, vol. 101, No. 3.

Kotsira, V.P. et al. "Oxalate Oxidase from Barley Roots: Purification to Homogeneity and Study of Some Molecular, Catalytic, and Binding Properties", *Arch. Biochem. Biophys.,* 1997, pp. 239–249, vol. 340, No .2.

Krebs, C. et al., "Mechanism of Rapid Electron Transfer During Oxygen Activation in the R2 Subunit of *eEscherichia coli* Ribonucleotide Reductase. 2. Evidence for and Consequences of Blocked Electron Transfer in the W48F Variant", *J. Am. Chem. Soc.,* 2000, pp. 12207–12219, vol. 122.

Kusnt, F. et al. "The Complete Genome Sequence of the Gram–Positive Bacterium *Bacillus subtilis*", *Nature,* 1997, pp. 249–256, vol. 390.

Landry, M.M. et al. "Calcium Oxalate Crystal Deposition in Necrotizing Otomycosis Caused by *Aspergillus niger*", *Mod. Pathol.,* 1993, pp. 493–496, vol. 6.

Lillehoj, E.B. et al. "An Oxalic Acid Decarboxylase of *Myrothecium Verrucaria*", *Arch. Biochem. Biophys.,* 1965, pp. 216–220, vol. 109.

Mehta, A. et al. "Oxalate Decarboxylase from *Collybia velutipes*—Purification, Characterization, and cDNA Cloning", *J. Biol. Chem.,* 1991, pp. 23548–23553, vol. 266, No. 35.

Metzger, J.B. et al., "Pulmonary Oxalosis Caused by *Aspergillus niger*", *Am. Rev. Respir. Dis.,* 1984, pp. 501–502, vol. 129.

Neves–Peterson, M.T. et al. "Engineering the pH–Optimum of a Triglyceride Lipase: From Predictions Based on Electrostatic Computations to Experimental Results", *J. Biotech.,* 2001, pp. 225–254, vol. 87.

Nielsen, J.E. et al. "Electrostatics in the Active Site of an α–Amylase", *Eur. J. Biochem.,* 1999, pp. 816–824, vol. 264.

Parast, C.V. et al. "Hydrogen Exchange of the Glycyl Radical of Pyruvate Formate–Lyase Is Catalyzed by Cysteine 419", *Biochemistry,* 1995, pp. 2393–2399, vol. 34, No. 8.

Parast, C.V. et al. "Electron Paramagnetic Resonance Evidence for a Cysteine–Based Radical in Pyruvate Formate–Lyase Inactivated with Mercaptopyruvate", *Biochemistry,* 1995, pp. 5712–5717, vol. 34.

Persson, A.L. et al. "Cysteinyl and Substrate Radical Formation in Active Site Mutant E441Q of *Escherichia coli* Class I Ribonucleotide Reductase",*J. Biol. Chem.,* 1998, pp. 31016–31020, vol. 273, No. 47.

Quayle, J.R. "Carbon Assimilation by *Pseudomonas oxalaticus* (OX1) Decarboxylation of Oxalyl–Coenzyme A to Formyl–Coenzyme A",*Biochem. J.,* 1963, pp. 492–503, vol. 89.

Requena, L. et al. "Barley (*Hordeum vulgare*) Oxalate Oxidase is a Manganese–Containing Enzyme", *Biochem. J.,* 1999, pp. 185–190, vol. 343.

Rupp, H. et al. "Electron Spin Relaxation of Iron–Sulphur Proteins Studied by Microwave Power Saturation", *Biochimica Biophysica Acta,* 1978, pp. 255–269, vol. 537.

Seebach, D. "Methods of Reactivity Umpolung", *Angew. Chem. Intl. Ed. Engl.,* 1979, pp. 239–258, vol. 18, No. 4.

Shaw, A. et al. "Protein Engineering of α–Amylase for Low pH Performance", *Current Opinion in Biotechnology,* 1999, pp. 349–352, vol. 10, No. 4.

Shimazono, H. "Oxalic Acid Decarboxylase, A New Enzyme from the Mycelium of Wood Destroying Fungi",*J. Biochem.,* 1955, pp. 321–340, vol. 42, No. 3.

Shimazono, H. et al. "Enzymatic Decarboxylation of Oxalic Acid", *J. Biol. Chem.,* 1957, pp. 151–159, vol. 227.

Solomons, C.C. et al. "Calcium Citrate for Vulvar Vestibulitus", *J. Repro. Med.,* 1991, pp. 879–882, vol. 36.

Su, Q. et al. "Probing the Mechanism of Proton Coupled Electron Transfer to Dioxygen: the Oxidative Half–Reaction of Bovine Serum Amine Oxidase", *Biochem,* 1998, pp. 12513–12525, vol. 37.

Tanner, A. et al. "*Bacillus subtilis* YvrK Is an Acid–Induced Oxalate Decarboxylase",*J. Bact.,* 2000, pp. 5271–5273, vol. 182, No. 18.

Tanner, A. et al. "Oxalate Decarboxylase Requires Manganese and Dioxygen for Activity", *J. Biol. Chem.,* 2001, pp. 43627–43634, vol. 276, No. 47.

Villafranca, J.J. et al. "Manganese (II) and Substrate Interaction with Unadenylylated Glutamine Synthetase (*Escherichia coli* W) II. Electron Paramagnetic Resonance and Nuclear Magnetic Resonance Studies of Enzyme–Bound Manganese(II) with Substrates and a Potential Transition-State Analogue, Methionine Sulfoximine", *Biochem.,* 1976, pp. 544–553, vol. 15, No. 3.

Walter, P. et al. "Signal Sequence Recognition and Protein Targeting to the Endoplasmic Reticulum Membrane", *Annu. Rev. Cell Biol.,* 19–94, pp. 87–119, vol. 10.

Woo, E. et al., "Germin is a Manganese Containing Homohexamer with Oxalate Oxidase and Superoxide Dismutase Activities", *Nat. Struct. Biol.,* 2000, pp. 1036–1040, vol. 7, No. 11.

Karlin, S. et al. "Methods for Assessing the Statistical Significance of Molecular Sequence Features by Using General Scoring Schemes", *Proc. Natl. Acad. Sci. USA,* 1990, pp. 2264–2268, vol. 87.

Karlin, S. et al. "Applications and Statistics for Multiple High–Scoring Segments in Molecular Sequences", *Proc. Natl. Acad. Sci. USA,* 1993, pp. 5873–5877, vol. 90.

Padmakumar, R. et al. "Evidence from Electron Paramagnetic Resonance Spectroscopy of the Participation of Radical Intermediates in the Reaction Catalyzed by Methymalonyl–Coenzyme A Mutase", *J. Biol. Chem.,* 1995, pp. 9295–9300, vol. 270, No. 16.

Drummond, A.Y. et al. "Stages in Oxidations of Organic Compounds by Potassium Permanganate: Part I. The Permanganate–Manganate Stage: Part II. The Manganic–Manganous Stage", *J. Biol. Soc.,* 1953, pp. 435–443.

Edlund, O. et al. "ENDOR Study of γ–Irradiated Single Crystals of Sodium Hydrogen Oxalate Monohydrate, $NaHC_2O_4H_2O$",*J. Magnetic Res.,* 1973, pp. 7–14, vol. 10.

Bard A.J. et al. "Electrode Potentials and Voltammetric Properties", *Encyclopedia of Electrochemistry of the Elements,* 1975, pp. 267–328, Marcel Dekker, Inc., New York.

* cited by examiner

```
  1 YQQLLQIPAS SPSIFFQDKP FTPDHRDPYD HKVDAIGEGH EPLPWRMGDG  50
 51 ATIMGPRNKD RERQNPDMLR PPSTDHGNMP NMRWSFADSH IRIEEGGWTR 100
101 QTTVRELPTS RELAGVNMRL DEGVIRELHW HREAEWAYVL AGRVRVTGLD 150
151 LEGGSFIDDL EEGDLWYFPS GHPHSLQGLS PNGTEFLLIF DDGNFSEEST 200
201 FLLTDWIAHT PKSVLAGNFR MRPQTFKNIP PSEKYIFQGS VPDSIPKELP 250
251 RNFKASKQRF THKMLAQEPE HTSGGEVRIT DSSNFPISKT VAAAHLTINP 299
300 GAIREMHWHP NADEWSYFKR GRARVTIFAA EGNARTFDYV AGDVGIVPRN 349
350 MGHFIENLSD DEEVEVLEIF RADRFRDFSL FQWMGETPQR MVAEHVFKDD 399
400 PDAAREFLKS VESGEKDPIR SPSE                            424
```

FIG. 2

```
             71                                                             130
genomic  TTACCAGCAA CTACTGCAGA TTCCCGCCTC ATCCCCATCC ATTTTCTTCC AAGACAAGCC
cDNA     TTACCAGCAA CTACTGCAGA TTCCCGCCTC ATCCCCATCC ATTTTCTTCC AAGACAAGCC
             1                                                              60

131                                                             190
genomic  ATTCACCCCC GATCATCGCG ACCCCTATGA TCACAAGGTG GATGCGATCG GGGAAGGCCA
cDNA     ATTCACCCCC GATCATCGCG ACCCCTATGA TCACAAGGTG GATGCGATCG GGGAAGGCCA
             61                                                            120

191                                                             250
genomic  TGAGCCCTTG CCCTGGCGCA TGGGAGATGG AGCCACCATC ATGGGACCCC GCAACAAGGA
cDNA     TGAGCCCTTG CCCTGGCGCA TGGGAGATGG AGCCACCATC ATGGGACCCC GCAACAAGGA
            121                                                            180

251                                                             310
genomic  CCGTGAGCGC CAGAACCCCG ACATGCTCCG TCCTCCGAGC ACCGACCATG GCAACATGCC
cDNA     CCGTGAGCGC CAGAACCCCG ACATGCTCCG TCCTCCGAGC ACCGACCATG GCAACATGCC
            181                                                            240

311                                                             370
genomic  CAACATGCGG TGGAGCTTTG CTGACTCCCA CATTCGCATT GAGGTAAGCC CTTCGAGAGT
cDNA     GAACATGCGG TGGAGCTTTG CTGACTCCCA CATTCGCATT GAG....... ..........
            241                                                            283

371                                                             430
genomic  CTTGTGTACG ACAAGCAAAA TAGGCTAATG CACTGCAGGA GGGCGGCTGG ACACGCCAGA
cDNA     .......... .......... .......... ........GA GGGCGGCTGG ACACGCCAGA
                                                   284                     305

431                                                             490
genomic  CTACCGTACG CGAGCTGCCA ACAAGCAGGG AGCTTGCTGG AGTAAACATG CGCCTTGATG
cDNA     CTACCGTACG CGAGCTGCCA ACAAGCAAGG AGCTTGCTGG AGTAAACATG CGCCTTGATG
            306                                                            365

491                                                             550
genomic  AGGGTGTCAT TCGCGAGCTG CACTGGCATC GGGAAGCACA GTGGGCGTAT GTGCTGGCCG
cDNA     AGGGTGTCAT TCGCGAGCTG CACTGGCATC GGGAAGCACA GTGGGCGTAT GTGCTGGCCG
            366                                                            425

551                                                             610
genomic  GACGTGTACG AGTGACTGGT CTTGACCTGG AGGGAGGCAG CTTCATCGAT GACCTGGAAG
cDNA     GACGTGTACG AGTGACTGGT CTTGACCTGG AGGGAGGCAG CTTCATCGAT GACCTGGAAG
            426                                                            485
```

FIG. 3A

```
                611                                                                         670
genomic   AGGGTGACCT CTGGTACTTC CCATCGGGCC ATCCCCATTC ACTTCAGGGT CTCAGTCCTA
cDNA      AGGGTGACCT CTGGTACTTC CCATCGGGCC ATCCCCATTC ACTTCAGGGT CTCAGTCCTA
                486                                                                         545

671                                                                         730
genomic   ATGGCACCGA GTTCTTACTG ATCTTCGACG ATGGAAACTT TTCCGAGGAG TCAACGTTCT
cDNA      ATGGCACCGA GTTCTTACTG ATCTTCGACG ATGGAAACTT TTCCGAGGAG TCAACGTTCT
                546                                                                         605

731                                                                         790
genomic   TGTTGACCGA CTGGATCGGT ATGTCCATCA CTATGCTGTT GTACAACCTC CACAAAAATA
cDNA      TGTTGACCGA CTGGATCG.. .......... .......... .......... ..........
                606        623

791                                                                         850
genomic   CTAACAATGC TATAAAACAG CACATACACC CAAGTCTGTC CTCGCCGGAA ACTTCCGCAT
cDNA      .......... .......... CACATACACC CAAGTCTGTC CTCGCCGGAA ACTTCCGCAT
                                      624                                                   663

851                                                                         910
genomic   GCGCCCACAA ACATTCAAGA ACATCCCACC ATCTGAAAAG TACATCTTCC AGGGCTCTGT
cDNA      GCGCCCACAA ACATTCAAGA ACATCCCACC ATCTGAAAAG TACATCTTCC AGGGCTCTGT
                664                                                                         723

911                                                                         970
genomic   CCCAGACTCT ATCCCCAAAG AACTTCCCCG CAACTTCAAA GCATCCAAGC AGCGCTTCAC
cDNA      CCCAGACTCT ATCCCCAAAG AACTTCCCCG CAACTTCAAA GCATCCAAGC AGCGCTTCAC
                724                                                                         783

971                                                                        1030
genomic   GCATAAGATG CTCGCTCAAG AACCCGAGCA TACCTCTGGC GGAGAGGTGC GCATCACAGA
cDNA      GCATAAGATG CTCGCTCAAG AACCCGAGCA TACCTCTGGC GGAGAGGTGC GCATCACAGA
                784                                                                         843

1031                                                                       1090
genomic   CTCGTCCAAC TTTCCCATCT CCAAGACGGT CGCGGCCGCC CACCTGACCA TTAACCCGGG
cDNA      CTCGTCCAAC TTTCCCATCT CCAAGACGGT CGCGGCCGCC CACCTGACCA TTAACCCGGG
                844                                                                         903

1091                                                                       1150
genomic   CGCTATCCGG GAGATGCACT GGCATCCCAA TGCGGATGAA TGGTCCTACT TTAAGCGCGG
cDNA      CGCTATCCGG GAGATGCACT GGCATCCCAA TGCGGATGAA TGGTCCTACT TTAAGCGCGG
                904                                                                         963

1151                                                                       1210
genomic   TCGGGCGCGA GTGACTATCT TCGCTGCTGA AGGTAATGCT CGTACATTCG ACTACGTAGC
cDNA      TCGGGCGCGA GTGACTATCT TCGCTGCTGA AGGTAATGCT CGTACATTCG ACTACGTAGC
                964                                                                        1023
```

FIG. 3B

```
         1211                                                            1270
genomic  GGGAGATGTG GGCATTGTTC CTCGCAACAT GGGTCATTTC ATTGAGAACC TCAGTGATGA
cDNA     GGGAGATGTG GGCATTGTTC CTCGCAACAT GGGTCATTTC ATTGAGAACC TCAGTGATGA
         1024                                                            1083

1271                                                            1330
genomic  CGAGGAGGTC GAGGTGTTGG AAATCTTCCG GGCGGACCGA TTCCGGGACT TTTCGTTGTT
cDNA     CGAGGAGGTC GAGGTGTTGG AAATCTTCCG GGCGGACCGA TTCCGGGACT TTTCGTTGTT
         1084                                                            1143

1331                                                            1390
genomic  CCAGTGGATG GGAGAGACGC CGCAGCGGAT GGTGGCAGAG CATGTGTTTA AGGATGATCC
cDNA     CCAGTGGATG GGAGAGACGC CGCAGCGGAT GCTGGCAGAG CATGTGTTTA AGGATGATCC
         1144                                                            1203

1391                                                            1450
genomic  AGATGCGGCC AGGGAGTTCC TTAAGAGTGT GGAGAGCGGG GAGAAGGATC CAATTCGGAG
cDNA     AGATGCGGCC AGGGAGTTCC TTAAGAGTGT GGAGAGCGGG GAGAAGGATC CGATTCGGAG
         1204                                                            1263

1451             1467
genomic  CCCAAGTGAG TAGATGA
cDNA     CCCAAGTGAG TAGATGA
         1264             1280
```

FIG. 3C

```
CTATGCATCC  AACGCGTTGG  GAGCTCTCCC  ATATGTCGA   CCTGCAGGCG  GCCGCGAATT  CACTAGTGAT
TTACCAGCAA  CTACTGCAGA  TTCCCGCCTC  ATCCCCATCC  ATTTTCTTCC  AAGACAAGCC  ATTCACCCCC
GATCATCGCG  ACCCCTATGA  TCACAAGGTG  GATGCGATCG  GGGAAGGCCA  TGAGCCCTTG  CCCTGGGCCA
TGGGAGATGG  AGCCACCATC  ATGGGACCCC  GCAACAAGGA  CCGTGAGCGC  CAGAACCCCG  ACATGCTCCG
TCCTCCGAGC  ACCGACCATG  GCAACATGCC  GAACATGCGG  TGGAGCTTTG  CTGACTCCCA  CATTCGCATT
GAGGTAAGCC  CTTCGAGAGT  CTTGTGTACG  ACAAGCAAAA  TAGGCTAATG  CACTGCAGGA  GGGCGGCTGG
ACACGCCAGA  CTACCGTACG  CGAGCTGCCA  ACAAGCAGGG  AGCTTGCTGG  AGTAAACATG  CGCCTTGATG
AGGGTGTCAT  TCGCGAGCTG  CACTGGCATC  GGGAAGCAGA  GTGGGCGTAT  GTGCTGGCCG  GACGTGTACG
AGTGACTGGT  CTTGACCTGG  AGGGAGGCAG  CTTCATCGAT  GACCTGGAAG  AGGTGACCT   CTGGTACTTC
CCATCGGGCC  ATCCCCATTC  ACTTCAGGGT  CTCAGTCCTA  ATGGCACCGA  GTTCTTACTG  ATCTTCGACG
ATGGAAACTT  TTCCGAGGAG  TCAACGTTCT  TGTTGACCGA  CTGGATCGGT  ATGTCCATCA  CTATGCTGTT
GTACAACCTC  CACAAAAATA  CTAACAATGC  TATAAAACAG  CACATACACC  CAAGTCTGTC  CTCGCCGGAA
ACTTCCGCAT  GCGCCCACAA  ACATTCAAGA  ACATCCCACC  ATCTGAAAAG  TACATCTTCC  AGGGCTCTGT
CCCAGACTCT  ATCCCCAAAG  AACTTCCCCG  CAACTTCAAA  GCATCCAAGC  AGCGCTTCAC  TTTCCATCT
CTCGCTCAAG  AACCCGAGCA  TACCTCTGGC  GGAGAGGTGC  GCATCACAGA  CTCGTCCAAC  GGCATCCCAA
CCAAGACGGT  CGCGGCCCGC  CACCTGACCA  TTAACCCGGG  CGCTATCCGG  GAGATGCACT  CGCATCTATCT
TGCGGATGAA  TGGTCCTACT  TTAAGCCCGG  TCGGGCCGCA  GTGACTATCT  TCGCTGCTGA  AGGTAATGCT
CGTACATTCG  ACTACGTAGC  GGGAGATGTG  GGCATTGTTC  CTCGCAACAT  GGTTCATTTC  ATTGAGAACC
TCAGTGATGA  CGAGGAGGTC  GAGGTGTTGG  AAATCTTCCG  GGCGGACCGA  TTCCGGGACT  TTTCGTTGTT
CCAGTGGATG  GGAGAGACGC  CGCAGCGGAT  GGTGGCAGAG  CATGTGTTTA  AGGATGATCC  AGATGCGGCC
AGGGAGTTCC  TTAAGAGTGT  GGAGAGCGGG  GAGAAGGATC  CCCAAGTGAG  TAGATGAAAT
CGAATTCCCG  CGGCCGCCAT  GGCGGCCGGG  AGCATGCGAC  GT (1512)
```

FIG. 4

```
  1 MKKQNDIPQP IRGDKGATVK IPRNIERDRQ NPDMLVPPET DHGTVSNMKF  50
 51 SFSDTHNRLE KGGYAREVTV RELPISENLA SVNMRLKPGA IRELHWHKEA 100
101 EWAYMIYGSA RVTIVDEKGR SFIDDVGEGD LWYFPSGLPH SIQALEEGAE 151
151 FLLVFDDGSF SENSTFQLTD WLAHTPKEVI AANFGVTKEE ISNLPGKEKY 200
201 IFENQLPGSL KDDIVEGPNG EVPYPFTYRL LEQEPIESEG GKVYIADSTN 250
251 FKVSKTIASA LVTVEPGAMR ELHWHPNTHE WQYYISGKAR MTVFASDGHA 299
300 RTFNYQAGDV GYVPFAMGHY VENIGDEPLV FLEIFKDDHY ADVSLNQWLA 349
350 MLPETFVQAH LDLGKDFTDV LSKEKHPVVK KKCSK                385
```

FIG. 5

SEQUENCE LISTING

<160> NUMBER OF SEQ ID NOS: 10

<210> SEQ ID NO 1
<211> LENGTH: 1397
<212> TYPE: DNA
<213> ORGANISM: Aspergillus niger

<400> SEQUENCE: 1

```
ttaccagcaa ctactgcaga ttcccgcctc atccccatcc attttcttcc aagacaagcc      60
attcaccccc gatcatcgcg acccctatga tcacaaggtg gatgcgatcg gggaaggcca     120
```

-continued

```
tgagcccttg ccctggcgca tgggagatgg agccaccatc atgggacccc gcaacaagga      180
ccgtgagcgc cagaaccccg acatgctccg tcctccgagc accgaccatg caacatgcc       240 gaacatgcgg tggagctttg ctgactccca cattcgcatt gaggtaagcc cttcgagagt      300
cttgtgtacg acaagcaaaa taggctaatg cactgcagga gggcggctgg acacgccaga     360
ctaccgtacg cgagctgcca acaagcaggg agcttgctgg agtaaacatg cgccttgatg     420
agggtgtcat tcgcgagctg cactggcatc gggaagcaga gtgggcgtat gtgctggccg     480
gacgtgtacg agtgactggt cttgacctgg agggaggcag cttcatcgat gacctggaag     540
agggtgacct ctggtacttc ccatcgggcc atccccattc acttcagggt ctcagtccta     600
atggcaccga gttcttactg atcttcgacg atggaaactt ttccgaggag tcaacgttct     660
tgttgaccga ctggatcggt atgtccatca ctatgctgtt gtacaacctc cacaaaaata     720
ctaacaatgc tataaaacag cacatacacc caagtctgtc ctcgccggaa acttccgcat     780
gcgcccacaa acattcaaga acatcccacc atctgaaaag tacatcttcc agggctctgt     840
cccagactct atccccaaag aacttccccg caacttcaaa gcatccaagc agcgcttcac     900
gcataagatg ctcgctcaag aacccgagca tacctctggc ggagaggtgc gcatcacaga    960
ctcgtccaac tttcccatct ccaagacggt cgcggccgcc cacctgacca ttaacccggg    1020
cgctatccgg gagatgcact ggcatcccaa tgcggatgaa tggtcctact ttaagcgcgg    1080
tcgggcgcga gtgactatct tcgctgctga agtaatgct cgtacattcg actacgtagc     1140
gggagatgtg ggcattgttc ctcgcaacat gggtcatttc attgagaacc tcagtgatga    1200
cgaggaggtc gaggtgttgg aaatcttccg ggcggaccga ttccgggact tttcgttgtt    1260
ccagtggatg ggagagacgc cgcagcggat ggtggcagag catgtgttta aggatgatcc    1320
agatgcggcc agggagttcc ttaagagtgt ggagagcggg gagaaggatc caattcggag    1380
cccaagtgag tagatga                                                    1397

<210> SEQ ID NO 2
<211> LENGTH: 1280
<212> TYPE: DNA
<213> ORGANISM: Aspergillus niger

<400> SEQUENCE: 2
ttaccagcaa ctactgcaga ttcccgcctc atccccatcc attttcttcc aagacaagcc      60
attcaccccc gatcatcgcg acccctatga tcacaaggtg gatgcgatcg gggaaggcca     120
tgagcccttg ccctggcgca tgggagatgg agccaccatc atgggacccc gcaacaagga     180
ccgtgagcgc cagaaccccg acatgctccg tcctccgagc accgaccatg caacatgcc      240 gaacatgcgg tggagctttg ctgactccca cattcgcatt gaggagggcg ctggacacg      300 ccagactacc gtacgcgagc tgccaacaag caaggagctt gctggagtaa acatgcgcct    360
tgatgagggt gtcattcgcg agctgcactg gcatcgggaa gcagagtggg cgtatgtgct    420
ggccggacgt gtacgagtga ctggtcttga cctggaggga ggcagcttca tcgatgacct    480
ggaagagggt gacctctggt acttcccatc gggccatccc cattcacttc agggtctcag   540
tcctaatggc accgagttct tactgatctt cgacgatgga aacttttccg aggagtcaac    600
gttcttgttg accgactgga tcgcacatac acccaagtct gtcctcgccg gaaacttccg    660
catgcgccca aaacattca agaacatccc accatctgaa aagtacatct tccagggctc    720
tgtcccagac tctatcccca aagaacttcc ccgcaacttc aaagcatcca agcagcgctt   780
```

-continued

```
cacgcataag atgctcgctc aagaacccga gcatacctct ggcggagagg tgcgcatcac    840
agactcgtcc aactttccca tctccaagac ggtcgcggcc gcccacctga ccattaaccc    900
gggcgctatc cgggagatgc actggcatcc caatgcggat gaatggtcct actttaagcg    960
cggtcgggcg cgagtgacta tcttcgctgc tgaaggtaat gctcgtacat tcgactacgt   1020
agcgggagat gtgggcattg ttcctcgcaa catgggtcat ttcattgaga acctcagtga   1080
tgacgaggag gtcgaggtgt tggaaatctt ccgggcggac cgattccggg acttttcgtt   1140
gttccagtgg atgggagaga cgccgcagcg gatggtggca gagcatgtgt taaggatga   1200 tccagatgcg gccagggagt tccttaagag tgtggagagc ggggagaagg atccgattcg   1260
gagcccaagt gagtagatga                                                1280
```

```
<210> SEQ ID NO 3
<211> LENGTH: 424
<212> TYPE: PRT
<213> ORGANISM: Aspergillus niger

<400> SEQUENCE: 3

Tyr Gln Gln Leu Leu Gln Ile Pro Ala Ser Ser Pro Ser Ile Phe Phe
1               5                   10                  15

Gln Asp Lys Pro Phe Thr Pro Asp His Arg Asp Pro Tyr Asp His Lys
            20                  25                  30

Val Asp Ala Ile Gly Glu Gly His Glu Pro Leu Pro Trp Arg Met Gly
        35                  40                  45

Asp Gly Ala Thr Ile Met Gly Pro Arg Asn Lys Asp Arg Glu Arg Gln
    50                  55                  60

Asn Pro Asp Met Leu Arg Pro Pro Ser Thr Asp His Gly Asn Met Pro
65                  70                  75                  80

Asn Met Arg Trp Ser Phe Ala Asp Ser His Ile Arg Ile Glu Glu Gly
                85                  90                  95

Gly Trp Thr Arg Gln Thr Thr Val Arg Glu Leu Pro Thr Ser Arg Glu
            100                 105                 110

Leu Ala Gly Val Asn Met Arg Leu Asp Glu Gly Val Ile Arg Glu Leu
        115                 120                 125

His Trp His Arg Glu Ala Glu Trp Ala Tyr Val Leu Ala Gly Arg Val
    130                 135                 140

Arg Val Thr Gly Leu Asp Leu Glu Gly Gly Ser Phe Ile Asp Asp Leu
145                 150                 155                 160

Glu Glu Gly Asp Leu Trp Tyr Phe Pro Ser Gly His Pro His Ser Leu
                165                 170                 175

Gln Gly Leu Ser Pro Asn Gly Thr Glu Phe Leu Leu Ile Phe Asp Asp
            180                 185                 190

Gly Asn Phe Ser Glu Glu Ser Thr Phe Leu Leu Thr Asp Trp Ile Ala
        195                 200                 205

His Thr Pro Lys Ser Val Leu Ala Gly Asn Phe Arg Met Arg Pro Gln
    210                 215                 220

Thr Phe Lys Asn Ile Pro Pro Ser Glu Lys Tyr Ile Phe Gln Gly Ser
225                 230                 235                 240

Val Pro Asp Ser Ile Pro Lys Glu Leu Pro Arg Asn Phe Lys Ala Ser
                245                 250                 255

Lys Gln Arg Phe Thr His Lys Met Leu Ala Gln Glu Pro Glu His Thr
            260                 265                 270

Ser Gly Gly Glu Val Arg Ile Thr Asp Ser Ser Asn Phe Pro Ile Ser
        275                 280                 285
```

```
Lys Thr Val Ala Ala His Leu Thr Ile Asn Pro Gly Ala Ile Arg
    290                 295                 300

Glu Met His Trp His Pro Asn Ala Asp Glu Trp Ser Tyr Phe Lys Arg
305                 310                 315                 320

Gly Arg Ala Arg Val Thr Ile Phe Ala Ala Glu Gly Asn Ala Arg Thr
                325                 330                 335

Phe Asp Tyr Val Ala Gly Asp Val Gly Ile Val Pro Arg Asn Met Gly
            340                 345                 350

His Phe Ile Glu Asn Leu Ser Asp Asp Glu Glu Val Glu Val Leu Glu
        355                 360                 365

Ile Phe Arg Ala Asp Arg Phe Arg Asp Phe Ser Leu Phe Gln Trp Met
    370                 375                 380

Gly Glu Thr Pro Gln Arg Met Val Ala Glu His Val Phe Lys Asp Asp
385                 390                 395                 400

Pro Asp Ala Ala Arg Glu Phe Leu Lys Ser Val Glu Ser Gly Glu Lys
                405                 410                 415

Asp Pro Ile Arg Ser Pro Ser Glu
                420

<210> SEQ ID NO 4
<211> LENGTH: 409
<212> TYPE: PRT
<213> ORGANISM: Aspergillus niger

<400> SEQUENCE: 4

Phe Gln Asp Lys Pro Phe Thr Pro Asp His Arg Asp Pro Tyr Asp His
1               5                   10                  15

Lys Val Asp Ala Ile Gly Glu Gly His Glu Pro Leu Pro Trp Arg Met
            20                  25                  30

Gly Asp Gly Ala Thr Ile Met Gly Pro Arg Asn Lys Asp Arg Glu Arg
        35                  40                  45

Gln Asn Pro Asp Met Leu Arg Pro Ser Thr Asp His Gly Asn Met
    50                  55                  60

Pro Asn Met Arg Trp Ser Phe Ala Asp Ser His Ile Arg Ile Glu Glu
65                  70                  75                  80

Gly Gly Trp Thr Arg Gln Thr Thr Val Arg Glu Leu Pro Thr Ser Arg
                85                  90                  95

Glu Leu Ala Gly Val Asn Met Arg Leu Asp Glu Gly Val Ile Arg Glu
            100                 105                 110

Leu His Trp His Arg Glu Ala Glu Trp Ala Tyr Val Leu Ala Gly Arg
        115                 120                 125

Val Arg Val Thr Gly Leu Asp Leu Glu Gly Gly Ser Phe Ile Asp Asp
    130                 135                 140

Leu Glu Glu Gly Asp Leu Trp Tyr Phe Pro Ser Gly His Pro His Ser
145                 150                 155                 160

Leu Gln Gly Leu Ser Pro Asn Gly Thr Glu Phe Leu Leu Ile Phe Asp
                165                 170                 175

Asp Gly Asn Phe Ser Glu Glu Ser Thr Phe Leu Leu Thr Asp Trp Ile
            180                 185                 190

Ala His Thr Pro Lys Ser Val Leu Ala Gly Asn Phe Arg Met Arg Pro
        195                 200                 205

Gln Thr Phe Lys Asn Ile Pro Pro Ser Glu Lys Tyr Ile Phe Gln Gly
    210                 215                 220

Ser Val Pro Asp Ser Ile Pro Lys Glu Leu Pro Arg Asn Phe Lys Ala
```

-continued

```
                225                 230                 235                 240
Ser Lys Gln Arg Phe Thr His Lys Met Leu Ala Gln Glu Pro Glu His
                245                 250                 255
Thr Ser Gly Gly Glu Val Arg Ile Thr Asp Ser Ser Asn Phe Pro Ile
            260                 265                 270
Ser Lys Thr Val Ala Ala Ala His Leu Thr Ile Asn Pro Gly Ala Ile
        275                 280                 285
Arg Glu Met His Trp His Pro Asn Ala Asp Glu Trp Ser Tyr Phe Lys
    290                 295                 300
Arg Gly Arg Ala Arg Val Thr Ile Phe Ala Ala Glu Gly Asn Ala Arg
305                 310                 315                 320
Thr Phe Asp Tyr Val Ala Gly Asp Val Gly Ile Val Pro Arg Asn Met
                325                 330                 335
Gly His Phe Ile Glu Asn Leu Ser Asp Asp Glu Val Glu Val Leu
            340                 345                 350
Glu Ile Phe Arg Ala Asp Arg Phe Arg Asp Phe Ser Leu Phe Gln Trp
        355                 360                 365
Met Gly Glu Thr Pro Gln Arg Met Val Ala His Val Phe Lys Asp
    370                 375                 380
Asp Pro Asp Ala Ala Arg Glu Phe Leu Lys Ser Val Glu Ser Gly Glu
385                 390                 395                 400
Lys Asp Pro Ile Arg Ser Pro Ser Glu
                405
```

```
<210> SEQ ID NO 5
<211> LENGTH: 21
<212> TYPE: DNA
<213> ORGANISM: Artificial sequence
<220> FEATURE:
<223> OTHER INFORMATION: PCR primer

<400> SEQUENCE: 5
gtcctcgaga aaagatacca g                                              21

<210> SEQ ID NO 6
<211> LENGTH: 27
<212> TYPE: DNA
<213> ORGANISM: Artificial sequence
<220> FEATURE:
<223> OTHER INFORMATION: PCR primer

<400> SEQUENCE: 6
tcatctactc acttgggctc cgaattg                                        27

<210> SEQ ID NO 7
<211> LENGTH: 11
<212> TYPE: PRT
<213> ORGANISM: Aspergillus niger

<400> SEQUENCE: 7

Phe Gln Asp Lys Pro Phe Thr Pro Asp His Arg
1               5                   10

<210> SEQ ID NO 8
<211> LENGTH: 4
<212> TYPE: PRT
<213> ORGANISM: Artificial sequence
<220> FEATURE:
<223> OTHER INFORMATION: Anticipated N-terminal sequence of oxalate
      decarboxylase of Aspergillus niger
```

```
<400> SEQUENCE: 8

Tyr Gln Gln Asp
1

<210> SEQ ID NO 9
<211> LENGTH: 385
<212> TYPE: PRT
<213> ORGANISM: Bacillus subtilis

<400> SEQUENCE: 9

Met Lys Lys Gln Asn Asp Ile Pro Gln Pro Ile Arg Gly Asp Lys Gly
1               5                   10                  15

Ala Thr Val Lys Ile Pro Arg Asn Ile Glu Arg Asp Arg Gln Asn Pro
            20                  25                  30

Asp Met Leu Val Pro Pro Glu Thr Asp His Gly Thr Val Ser Asn Met
        35                  40                  45

Lys Phe Ser Phe Ser Asp Thr His Asn Arg Leu Glu Lys Gly Gly Tyr
    50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Ile Val Glu Gly Pro Asn Gly Glu Val Pro Tyr
    210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
            260                 265                 270

His Trp His Pro Asn Thr His Glu Trp Gln Tyr Tyr Ile Ser Gly Lys
        275                 280                 285

Ala Arg Met Thr Val Phe Ala Ser Asp Gly His Ala Arg Thr Phe Asn
    290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350
```

```
Pro Glu Thr Phe Val Gln Ala His Leu Asp Leu Gly Lys Asp Phe Thr
        355                 360                 365

Asp Val Leu Ser Lys Glu Lys His Pro Val Val Lys Lys Lys Cys Ser
    370                 375                 380

Lys
385

<210> SEQ ID NO 10
<211> LENGTH: 1512
<212> TYPE: DNA
<213> ORGANISM: Aspergillus niger

<400> SEQUENCE: 10
ctatgcatcc aacgcgttgg gagctctccc atatggtcga cctgcaggcg gccgcgaatt    60
cactagtgat ttaccagcaa ctactgcaga ttcccgcctc atccccatcc attttcttcc   120
aagacaagcc attcaccccc gatcatcgcg accccttatga tcacaaggtg gatgcgatcg   180
gggaaggcca tgagcccttg ccctggcgca tgggagatgg agccaccatc atgggacccc   240
gcaacaagga ccgtgagcgc cagaaccccg acatgctccg tcctccgagc accgaccatg   300
gcaacatgcc gaacatgcgg tggagctttg ctgactccca cattcgcatt gaggtaagcc   360
cttcgagagt cttgtgtacg acaagcaaaa taggctaatg cactgcagga gggcggctgg   420
acacgccaga ctaccgtacg cgagctgcca acaagcaggg agcttgctgg agtaaacatg   480
cgccttgatg agggtgtcat tcgcgagctg cactggcatc gggaagcaga gtgggcgtat   540
gtgctggccg gacgtgtacg agtgactggt ctttgacctgg agggaggcag cttcatcgat   600
gacctggaag agggtgacct ctggtacttc ccatcgggcc atccccattc acttcagggt   660
ctcagtccta atggcaccga gttcttactg atcttcgacg atggaaactt ttccgaggag   720
tcaacgttct tgttgaccga ctggatcggt atgtccatca ctatgctgtt gtacaacctc   780
cacaaaaata ctaacaatgc tataaaacag cacatacacc caagtctgtc ctcgccggaa   840
acttccgcat gcgcccacaa acattcaaga acatcccacc atctgaaaag tacatcttcc   900
agggctctgt cccagactct atccccaaag aacttccccg caacttcaaa gcatccaagc   960
agcgcttcac gcataagatg ctcgctcaag aacccgagca tacctctggc ggagaggtgc  1020
gcatcacaga ctcgtccaac tttcccatct ccaagacggt cgcggccgcc cacctgacca  1080
ttaacccggg cgctatccgg gagatgcact ggcatcccaa tgcggatgaa tggtcctact  1140
ttaagcgcgg tcgggcgcga gtgactatct tcgctgctga aggtaatgct cgtacattcg  1200
actacgtagc gggagatgtg ggcattgttc ctcgcaacat gggtcatttc attgagaacc  1260
tcagtgatga cgaggaggtc gaggtgttgg aaatcttccg ggcggaccga ttccgggact  1320
tttcgttgtt ccagtggatg ggagagacgc cgcagcggat ggtggcagag catgtgttta  1380
aggatgatcc agatgcggcc agggagttcc ttaagagtgt ggagagcggg gagaaggatc  1440
caattcggag cccaagtgag tagatgaaat cgaattcccg cggccgccat ggcggccggg  1500
agcatgcgac gt                                                       1512
```

POLYNUCLEOTIDES ENCODING OXALATE DECARBOXYLASE FROM *ASPERGILLUS NIGER* AND METHODS OF USE

CROSS-REFERENCE TO RELATED APPLICATION

This application claims the benefit of U.S. Provisional Application Ser. No. 60/404,892, filed Aug. 20, 2002.

The subject invention was made with government support under a research project supported by National Institutes of Health Grant No. DK53556.

BACKGROUND OF THE INVENTION

Oxalic acid, a compound that is toxic to almost all organisms (Hodgkinson, 1977), plays several important roles in fungal growth and metabolism (Dutton et al., 1996), and in biological mechanisms underlying fungal pathogenesis. For example, *Aspergillus niger*, which can colonize lung tissue in immunocompromised individuals, excretes enough oxalate to form crystalline calcium salts as part of necrotizing otomycosis (Landry et al., 1993) and, in certain cases, can give rise to fatal pulmonary oxalosis (Kimmerling et al., 1992; Metzger et al., 1984). A number of enzymes have evolved in plants (oxalate oxidase) (Kotsira et al., 1997), fungi (oxalate decarboxylase) (Lillehoj et al., 1965) and bacteria (oxalyl-CoA decarboxylase) (Quayle, 1963) to remove oxalate from the environment. Oxalate decarboxylase (OxDC) catalyzes a remarkable transformation in which the C—C bond in oxalate is cleaved to give carbon dioxide and formate:

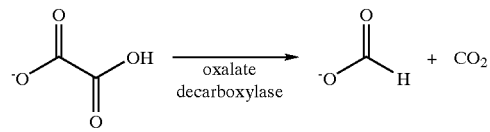

The enzyme is presumably important in fungal metabolism as a protective agent against internalization of neutral oxalate formed in the environment as the soil pH drops due to wood degradation or secretion of oxalic acid. Oxalate decarboxylase was first isolated from basidiomycete fungi (Shimazono, 1955), and has subsequently been identified in several species of filamentous fungi, including *Myrothecium verrucaria* (Lillehoj et al., 1965), certain strains of *Aspergillus niger* (Emiliani et al., 1964) and *Flammulina velutipes* (Mehta et al., 1991), and the common button mushroom *Agaricus bisporus* (Kathiara et al., 2000). OxDC expression can also be induced in the white-rot fungus *Coriolus versicolor* (Shimazono et al., 1957), and very recent work has also shown that OxDC is present in *Bacillus subtilis* (Tanner et al., 2000), although this appears to be the only bacterium in which the presence of this enzyme has been unambiguously demonstrated. While it has been demonstrated that the bacterial OxDC is manganese-dependent (Tanner et al., 2001), the detailed catalytic mechanism by which oxalate is converted to formate and carbon dioxide has not yet been elucidated.

Early experiments employing the *Aspergillus niger* OxDC showed that (i) enzymatic $CO_2$ evolution requires oxalate to the exclusion of other biologically relevant carboxylic acids, (ii) oxygen is required for catalytic turnover, although high oxygen tensions inhibit the enzyme (Emiliani et al., 1968), and (iii) a sub-stoichiometric quantity of oxygen is converted to hydrogen peroxide during the reaction. Weak reductants such as phenylenediamines and diphenols activate the enzyme, whereas treatment with strong reductants such as dithionite and hydroxylamine eliminate OxDC activity. No evidence was found for the presence of exogenous cofactors in the native *Aspergillus niger* OxDC, and the enzyme was reported not to contain iron and copper ions as purified. A general, oxygen-dependent, mechanism involving the formation of free radical species was proposed to account for these experimental observations (Emiliani et al., 1968). In light of the demonstrated dependence of OxDC activity on dioxygen (Tanner et al., 2001), a hypothetical catalytic mechanism is currently favored in which bound manganese undergoes an oxidation to give a species capable of abstracting an electron directly from oxalate to give the radical anion 1 (Scheme 1A). It is also likely that oxalate binding to manganese precedes that of dioxygen. C—C bond cleavage, which might be expected to be a fast chemical step, then yields 2 and concomitant proton and electron transfer (Su et al., 1998) to give formate regenerates the oxidized metal species. No evidence for the involvement of a redox-active co-factor (Halcrow, 2001) is provided by the recent crystal structure of the bacterial OxDC (Anand et al., 2002). The structures of the fungal and bacterial oxalate decarboxylases are likely to be very similar on the basis of sequence identity and the likely evolutionary relationship between the two enzymes (Dunwell et al., 2000). The observed correlation between $H_2O_2$ formation and $pO_2$ in the OxDC-catalyzed reaction (Emiliani et al., 1968) is consistent with such a mechanism if oxidation of the formyl radical anion 2 takes place to generate $CO_2$, peroxide anion and an inactive form of OXDC (Scheme 1B).

Scheme 1

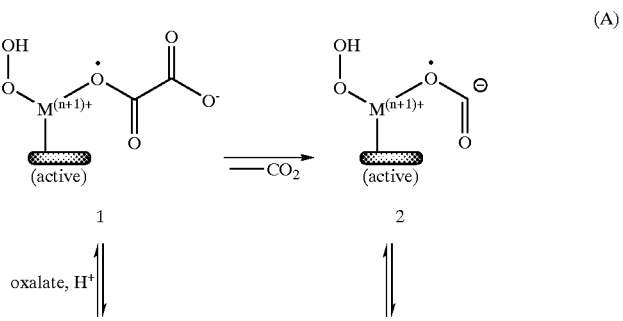

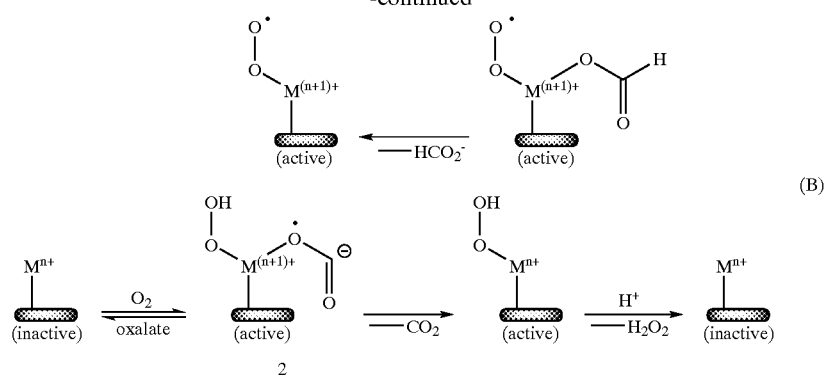

(A) Hypothetical mechanism for OxDC-catalyzed conversion of oxalate into $CO_2$ and formulate via homolytic C——C bond cleavage.

Note that the interaction of the manganese ion ($Mn^+$) with oxygen and oxalate remains to be established experimentally.

(B) Side reaction proposed to consume oxygen during turnover.

Although it has been speculated that Mn(III) and Mn(IV) are the redox active forms of the metal during catalysis (Anand et al., 2002), there is no published evidence to support such a claim. Equally, the intermediacy of a protein-based radical cannot be ruled out on the basis of current biochemical and structural information on *Bacillus subtilis* OxDC. This proposal has the merit of rationalizing the observed correlation between the amounts of hydrogen peroxide formed under the assay conditions and the partial pressure of oxygen. Chemical precedent for a mechanism involving radical-dependent decarboxylation of oxalate has been obtained in model chemical studies (Drummond et al., 1953; Halliwell, 1972), including direct electron-nuclear double resonance (ENDOR) observation of formate radical produced by irradiation of oxalate crystals (Edlund et al., 1973). Additional support is provided by the Kolbe reaction in which one-electron electrochemical oxidation of carboxylic acids results in production of $CO_2$ and daughter radicals (Bard et al., 1978). Nevertheless, a radical-based mechanism for OxDC-catalyzed oxalate degradation would gain considerable credence upon observation of paramagnetic species formed on incubation of the enzyme with substrate.

Kidney-urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease, cardiac conductance disorders, Crohn's disease, and other enteric disease states.

Oxalic acid (and/or its salt-oxalate) is found in a wide diversity of foods, and is therefore, a component of many constituents in human and animal diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate. In addition, compliance with a low oxalate diet is often problematic.

Normal tissue enzymes also produce endogenous oxalate metabolically. Oxalate (dietary oxalate that is absorbed as well as oxalate that is produced metabolically) is not further metabolized by tissue enzymes and must therefore be excreted. This excretion occurs mainly via the kidneys. The concentration of oxalate in kidney fluids is critical, with increased oxalate concentrations causing increased risk for the formation of calcium oxalate crystals and thus the subsequent formation of kidney stones.

The risk for formation of kidney stones revolves around a number of factors that are not yet completely understood. Kidney-urinary tract stone disease occurs in as much as 12% of the population in Western countries and about 70% of these stones are composed of calcium oxalate or of calcium oxalate plus calcium phosphate. Some individuals (e.g., patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in man, is known as enteric hyperoxaluria. Oxalate is also a problem in patients with end-stage renal disease and there is recent evidence (Solomons et al, 1991) that elevated urinary oxalate is also involved in vulvar vestibulitis (vulvodynia).

Bacteria that degrade oxalate have been isolated from human feces (Allison et al., 1986). These bacteria were found to be similar to oxalate-degrading bacteria that had been isolated from the intestinal contents of a number of species of animals (Dawson et al., 1980; Allison et al., 1981; Daniel et al., 1987). These bacteria are different from any previously described organism and have been given both a new species and a new genus name (Allison et al., 1985).

Not all humans carry populations of *O. formigenes* in their intestinal tracts (Allison et al., 1995; Doane et al, 1989). There are low concentrations or a complete lack of oxalate degrading bacteria in the fecal samples of persons who have had jejunoileal bypass surgery (Allison et al., 1986). Also, certain humans and animals may maintain colonies of *O. formigenes* but nevertheless have excess levels of oxalate for reasons that are not clearly understood.

U.S. Pat. No. 6,355,242 and published international patent application WO 98/52586 disclose delivery of bacteria and/or oxalate-degrading enzymes to intestinal tracts of persons or animals, thereby reducing oxalate in the intestinal tract of those persons or animals who are at risk for oxalate related disease.

OxDC of *Aspergillus niger*, which converts oxalate directly to formate and carbon dioxide without the need for exogenous co-factors, can provide a therapeutic approach at a significant reduction in cost. A second benefit of using *Aspergillus niger* OxDC is that the enzyme has a pH-optimum of 4.2, making it useful for oxalate degradation in the upper intestine. Since *Aspergillus niger* is also used in the production of citrate, which is then added to food products and dietary supplements, it is likely that no significant side effects will be observed when this form of OxDC is administered in the human gastrointestinal tract.

BRIEF SUMMARY OF THE INVENTION

The subject invention pertains to polynucleotides encoding the enzyme oxalate decarboxylase from the filamentous fungus *Aspergillus niger* and methods of use. The polynucleotides can be used to express oxalate *Aspergillus niger* decarboxylase that can be used to degrade oxalate for therapeutic and other purposes. The subject invention also pertains to cells and microbes, such as bacteria, which are transformed with a polynucleotide of the present invention encoding an oxalate decarboxylase enzyme.

The subject invention also pertains to plants that are transformed with a polynucleotide of the present invention encoding an oxalate decarboxylase enzyme. Transformed plants of the present invention expressing oxalate decarboxylase can be administered to a human or animal as a constituent of a meal, for example, as a salad or vegetable. In addition, the transformed plant of the present invention can be administered to an animal as a constituent of feed or the plant can be grown in a pasture in which animals are allowed to graze and feed upon the plant.

The subject invention also concerns the use of *Aspergillus niger* oxalate decarboxylase, or a microbe transformed with a polynucleotide of the invention to express oxalate decarboxylase of the invention, to achieve therapeutic oxalate degradation in a human or animal.

The subject invention also pertains to use of oxalate decarboxylase of the invention to degrade oxalate present in fluids, such as blood and urine. For example, oxalate decarboxylase of the invention can be coated or attached to a surface, for example, that of a catheter or other medical device, that might come into contact with a fluid containing oxalate. The attached enzyme can prevent oxalate accumulation or encrustation on those surfaces of a device that are in contact with the fluid.

BRIEF DESCRIPTION OF DRAWINGS

FIG. 2 shows the deduced primary structure of *Aspergillus niger* oxalate decarboxylase protein (SEQ ID NO. 3) from the cDNA sequence shown in FIG. 3. Amino acids that define the signal peptide of the protein are shown in italic font. Standard one letter code is used to represent amino acids.

FIGS. 3A–C shows the alignment of the nucleotide sequences of the gene encoding oxalate decarboxylase *Aspergillus niger* (genomic) OxDC (SEQ ID NO. 1) and the cDNA (SEQ ID NO. 2) obtained from mRNA isolated from the fungus (cDNA). Underlined residues in the genomic sequence indicate the location of the two introns deduced to be present in the gene by comparison of the sequences. These are both flanked by canonical sequences shown in bold typeface. The TAG sequence at the 3'-end of the gene, also showing bold typeface, indicates the end of the region coding for the protein product.

FIG. 4 shows the DNA sequence (SEQ ID NO. 10) encoding oxalate decarboxylase as cloned from genomic DNA of *Aspergillus niger*.

FIG. 5 shows the deduced primary structure of *Bacillus subtilus* yvrk protein (SEQ ID NO. 9). Standard one letter code is used to represent amino acids.

BRIEF DESCRIPTION OF SEQUENCES

Figure 1:
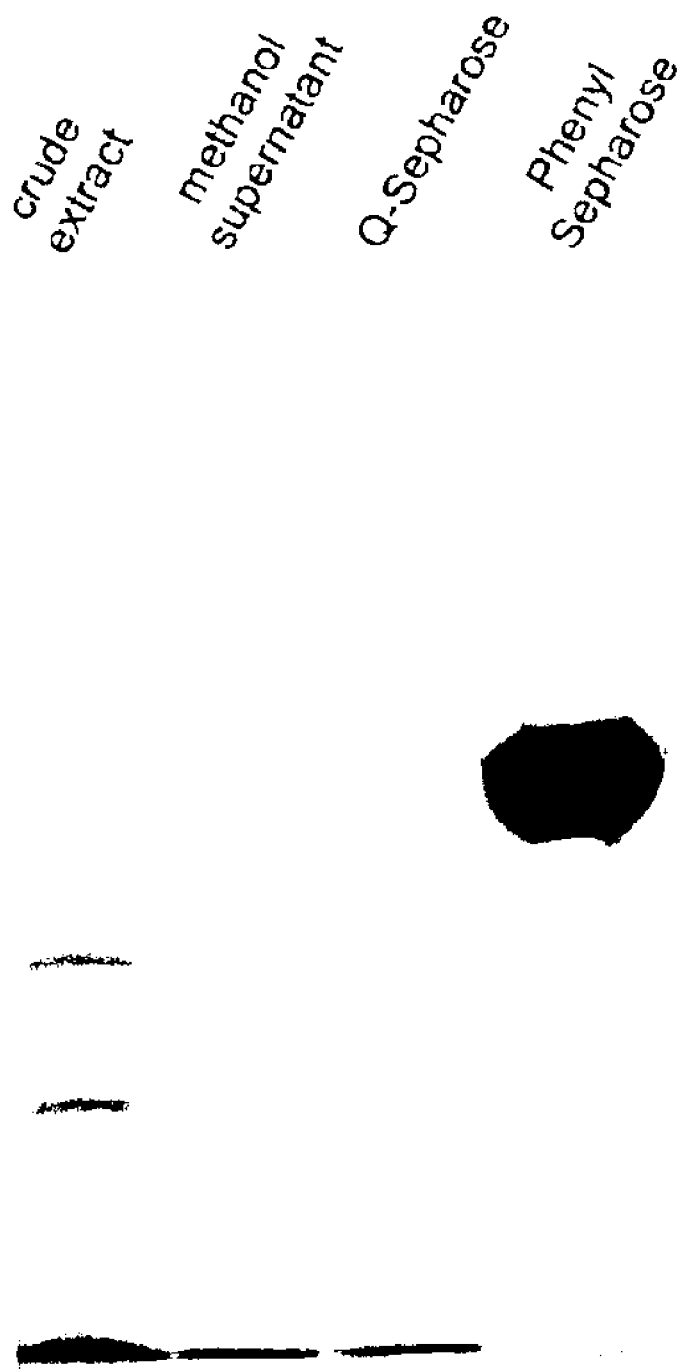
FIG. 1 shows an SDS-PAGE gel of oxalate decarboxylase purification fractions obtained from the procedures described in "Materials and Methods" section herein. Lanes from left to right are crude extract, methanol re-suspension, Q-Sepharose fractions and phenyl Sepharose fractions.

SEQ ID NO. 1 is a genomic polynucleotide of *Aspergillus niger* encoding an oxalate decarboxylase enzyme that can be used according to the present invention.

SEQ ID NO. 2 is a cDNA sequence of *Aspergillus niger* encoding an oxalate decarboxylase enzyme that can be used according to the present invention.

SEQ ID NO. 3 is the amino acid sequence of an oxalate decarboxylase enzyme of *Aspergillus niger* encoded by SEQ ID NO. 1.

SEQ ID NO. 4 is an amino acid sequence of an oxalate decarboxylase enzyme of the invention with the amino acid leader sequence removed.

SEQ ID NO. 5 is a sequence of a PCR primer that can be used according to the present invention.

SEQ ID NO. 6 is a sequence of a PCR primer that can be used according to the present invention.

SEQ ID NO. 7 is a partial sequence of the oxalate decarboxylase enzyme of the present invention.

SEQ ID NO. 8 is a predicted partial sequence of the oxalate decarboxylase enzyme of the present invention.

SEQ ID NO. 9 is the deduced primary structure of *Bacillus subtilis* yvrk protein according to the present invention.

DETAILED DISCLOSURE OF THE INVENTION

The subject invention concerns polynucleotides encoding the enzyme oxalate decarboxylase from the filamentous fungus *Aspergillus niger*. The amino acid sequence of the oxalate decarboxylase enzyme from *Aspergillus niger* is shown in FIG. 2 (SEQ ID NO. 3). The subject invention pertains to the enzyme having the sequence shown in FIG. 2 (SEQ ID NO. 3), as well as the enzyme lacking the leader sequence (shown in italics in FIG. 2), i.e., a polypeptide of SEQ ID NO 4. A cDNA sequence that encodes the oxalate decarboxylase enzyme from *Aspergillus niger* is shown in the bottom row of nucleotide sequence in FIG. 3 (SEQ ID NO. 2). The genomic sequence from *Aspergillus niger* encoding oxalate decarboxylase is shown in the top row of nucleotide sequence in FIG. 3 (SEQ ID NO. 1). The subject invention also concerns the polypeptides of the invention complexed with a metal. Preferably, the metal is manganese, iron, or copper. More preferably, the metal is manganese.

The subject invention also concerns pharmaceutical and nutraceutical compositions for the introduction of the oxalate decarboxylase of the present invention and/or bacteria or other cells that have been transformed with a polynucleotide of the present invention into the intestine of a human or animal. In one embodiment, the transformed bacteria or cell or enzyme has been lyophilized or frozen. A liquid or paste form can be encapsulated in a gel capsule or provided with other forms of enteric protection. Preferably, the gel capsule material or the material providing enteric protection is resistant to degradation by the acidity and enzymes of the stomach but can be degraded, with concomitant release of the enzyme and/or transformed bacteria or cell of the invention, by the higher pH and bile acid contents present in the human or animal intestinal tract.

The subject invention also concerns transgenic animals in which a polynucleotide encoding an oxalate decarboxylase of the invention has been incorporated into the animal's genome. Methods for preparing transgenic animals are well known in the art.

The subject invention also concerns an enzyme delivery system comprising a plant which has been transformed with a polynucleotide of the subject invention encoding oxalate decarboxylase, which when expressed can degrade oxalate. Transformed plants of the present invention expressing oxalate decarboxylase can be administered to a human or animal as a constituent of a meal, for example, as a salad or vegetable. In addition, the transformed plant of the present invention can be administered to an animal as a constituent of feed or the plant can be grown in a pasture in which animals are allowed to graze and feed upon the plant.

The subject application also concerns plants transformed with polynucleotides of the present invention that encode oxalate decarboxylase from *Aspergillus niger*. Plants that can be transformed with the subject polynucleotide include both monocotyledonous and dicotyledonous plants. Plants within the scope of the present invention include monocotyledonous plants, such as rice, wheat, barley, oats, sorghum, maize, lilies, and millet, and dicotyledonous plants, such as peas, alfalfa, chickpea, chicory, clover, kale, lentil, prairie grass, soybean, tobacco, potato, sweet potato, radish, cabbage, rape, apple trees, and lettuce. In a particularly preferred embodiment, the plant is a cereal. Cereals to which this invention applies include, for example, maize, wheat, rice, barley, oats, rye, and millet.

The subject invention also concerns methods for degrading oxalate present in fluids, such as blood and urine, using oxalate decarboxylase of the present invention. The subject invention can be used to prevent or minimize encrustation of oxalate crystals on any device, such as a catheter, that comes into contact with oxalate-containing fluids. An oxalate decarboxylase enzyme of the invention can be provided on or in any devices that come into contact with fluids that contain or may contain oxalate. For example, the enzyme can be coated to or attached on the inside of a medical catheter or stent. The enzyme could also be provided in dialysis cartridges to degrade oxalate present in a patient's biological fluid.

The subject invention also concerns methods and compositions for assaying for the presence of oxalate. In one embodiment, the method comprises contacting a sample to be assayed with an oxalate decarboxylase of the present invention and then determining the presence of either carbon dioxide or formate generated from the reaction of the enzyme with oxalate.

The subject invention also concerns pharmaceutical and nutraceutical compositions for the introduction of the oxalate decarboxylase of *Bacillus subtilis* and/or bacteria or other cells that have been transformed with a polynucleotide encoding the oxalate decarboxylase of *Bacillus subtilis* into the intestine of a human or animal. In one embodiment, the transformed bacteria or cell or enzyme has been lyophilized or frozen. A liquid or paste form can be encapsulated in a gel capsule or provided with other forms of enteric protection. Preferably, the gel capsule material or the material providing enteric protection is resistant to degradation by the acidity and enzymes of the stomach but can be degraded, with concomitant release of the enzyme and/or transformed bacteria or cell of the invention, by the higher pH and bile acid contents present in the human or animal intestinal tract.

The subject invention also concerns transgenic animals in which a polynucleotide encoding oxalate decarboxylase of *Bacillus subtilis* has been incorporated into the animal's genome. Methods for preparing transgenic animals are well known in the art.

The subject invention also concerns an enzyme delivery system comprising a plant which has been transformed with a polynucleotide encoding oxalate decarboxylase of *Bacillus subtilis*, which when expressed can degrade oxalate. Transformed plants of the present invention expressing oxalate decarboxylase of *Bacillus subtilis* can be administered to a human or animal as a constituent of a meal, for example, as a salad or vegetable. In addition, the transformed plant of the present invention can be administered to an animal as a constituent of feed or the plant can be grown in a pasture in which animals are allowed to graze and feed upon the plant.

The subject application also concerns plants transformed with polynucleotides encoding the oxalate decarboxylase of *Bacillus subtilis*. Plants that can be transformed with the subject polynucleotide include both monocotyledonous and dicotyledonous plants. Plants within the scope of the present invention include monocotyledonous plants, such as rice, wheat, barley, oats, sorghum, maize, lilies, and millet, and dicotyledonous plants, such as peas, alfalfa, chickpea, chicory, clover, kale, lentil, prairie grass, soybean, tobacco, potato, sweet potato, radish, cabbage, rape, apple trees, and lettuce. In a particularly preferred embodiment, the plant is a cereal. Cereals to which this invention applies include, for example, maize, wheat, rice, barley, oats, rye, and millet.

The subject invention also concerns methods for degrading oxalate present in fluids, such as blood and urine, using oxalate decarboxylase of *Bacillus subtilis*. The subject invention can be used to prevent or minimize encrustation of oxalate crystals on any device, such as a catheter, that comes into contact with biological fluids. Oxalate decarboxylase of *Bacillus subtilis* can be provided on or in any devices that come into contact with fluids that contain or may contain oxalate. For example, the enzyme can be coated to or attached on the inside of a medical catheter or stent. The enzyme could also be provided in dialysis cartridges to degrade oxalate present in a patient's biological fluid.

The methods and compositions of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

Polynucleotides of the present invention can be composed of either RNA or DNA. Preferably, the polynucleotides are composed of DNA. The subject invention also encompasses those polynucleotides that are complementary in sequence to the polynucleotides disclosed herein.

Because of the degeneracy of the genetic code, a variety of different polynucleotide sequences can encode oxalate decarboxylase enzymes disclosed herein. In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences that encode amino acid substitutions, deletions, additions, or insertions, which do not materially alter the functional activity of the polypeptide, encoded by the polynucleotides of the present invention.

Substitution of amino acids other than those specifically exemplified in the sequence of oxalate decarboxylase disclosed herein is also contemplated within the scope of the present invention. Amino acids can be placed in the following classes: non-polar, uncharged polar, basic, and acidic. Conservative substitutions whereby an oxalate decarboxylase polypeptide having an amino acid of one class is replaced with another amino acid of the same class fall within the scope of the subject invention so long as the oxalate decarboxylase having the substitution still retains substantially the same activity as wild type polypeptide. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Also contemplated are substitutions of naturally occurring amino acids in the oxalate decarboxylase sequence with non-natural amino acids. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The scope of the invention also includes amino acid substitutions in the sequence of the polypeptide that change the pH optimum at which the polypeptide exhibits the highest level of enzymatic activity. Techniques for making such amino acid substitutions and assaying the polypeptide for pH optimum are well known in the art (Neves-Peterson et al., 2001; Nielson et al., 1999; Shaw et al., 1999).

Polynucleotides and proteins of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also concerns polynucleotides, which encode fragments of a full-length oxalate decarboxylase enzyme of the invention, so long as those fragments retain substantially the same functional activity as full-length polypeptide. The fragments of an oxalate decarboxylase polypeptide encoded by these polynucleotides are also within the scope of the present invention. Fragments of the full-length sequence can be prepared using standard techniques known in the art.

The subject invention also contemplates those polynucleotide molecules encoding oxalate decarboxylase enzymes having sequences that are sufficiently homologous with the wild type sequence of *Aspergillus niger* so as to permit hybridization with that sequence under standard stringent conditions and standard methods (Maniatis et al., 1982). As used herein, "stringent" conditions for hybridization refers to conditions wherein hybridization is typically carried out overnight at 20–25 C below the melting temperature (Tm) of the DNA hybrid in 6×SSPE, 5× Denhardt's solution, 0.1% SDS, 0.1 mg/ml denatured DNA. The melting temperature is described by the following formula (Beltz et al., 1983):

$$Tm=81.5\ C+16.6\ Log[Na+]+0.41(\%\ G+C)-0.61(\%\ formamide)-600/\text{length of duplex in base pairs.}$$

Washes are typically carried out as follows:
(1) Twice at room temperature for 15 minutes in 1×SSPE, 0.1% SDS (low stringency wash).
(2) Once at Tm−20 C for 15 minutes in 0.2×SSPE, 0.1% SDS (moderate stringency wash).

All patents, patent applications, provisional applications, and publications referred to or cited herein are incorporated by reference in their entirety to the extent they are not inconsistent with the explicit teachings of this specification.

Materials and Methods

Culture Conditions. *Aspergillus niger* (ATCC 26550) was maintained on potato dextrose agar plates at 4° C. Inoculating a starter culture of ATCC medium 950 with a loopful of *Aspergillus niger* spores produced mycelium for OXDC purification. The literature procedures for inducing OxDC production were modified by the substitution of sucrose for glucose (by weight), $NH_4Cl$ for $NaNO_3$ (by molarity) and the addition of 10 mM sodium oxalate (Sigma). After growth at 30° C. for several days, this starter culture was used to inoculate larger cultures. Fungus for DNA isolation was grown on yeast extract-peptone-dextrose medium (ATCC medium 1005), with cultures being shaken at 37° C. until the mycelium was confluent. Mycelium was harvested by vacuum filtration, washed with de-ionized water, frozen in powdered dry ice, lyophilized, and stored at −80° C. until used in subsequent experiments.

Isolation of Native OXDC. Freeze-dried mycelium was ground in a mortar and pestle with powdered dry ice. After sublimation, the powder was suspended in 20 mM NaOAc pH 5.6 buffer plus 0.1% Tween 20. Insoluble material was removed by centrifugation, and methanol added to the supernatant to a final concentration of 50% v/v. The resulting mixture was incubated at 0° C. for 30 minutes before collection of precipitated material by centrifugation. The pellet was re-suspended in 20 mM NaOAc pH 5.6 ("purification buffer") and incubated overnight at 4° C. Insoluble material was again removed by centrifugation, and the supernatant applied to a 1.6×12.5 cm Q-Sepharose Hi-Performance column (Amersham Pharmacia Biotech). The column was washed with purification buffer, and then eluted with a 0–1 M NaCl gradient. Active fractions were pooled, before the addition of solid $(NH_4)_2SO_4$ to a final concentration of 1 M. After re-suspension and loading onto a 1.6×12 cm Phenyl Sepharose Hi-Performance column, bound protein was washed with purification buffer containing 1 M $(NH_4)_2SO_4$, then eluted with a 1–0 M ammonium sulfate gradient. Active fractions were pooled, diafiltered and concentrated, and stored at 4° C. prior to characterization. Additional details of this purification procedure are shown in Table 2.

TABLE 2

Purification of *Aspergillus niger* oxalate decarboxylase

| Fraction | Activity (nmol/min) | Specific Activity (I.U./mg) | Total Activity (I.U.) | Fold-Purification | % Yield |
|---|---|---|---|---|---|
| Crude extract | 1.4 | 0.02 | 51 | | |
| Methanol Supernatant | 8.8 | 0.52 | 88 | 34 | 100* |
| Q Sepharose | 5.4 | 5.7 | 33 | 376 | 37 |
| Phenyl Sepharose | 9.2 | 10 | 18 | 662 | 21 |

Enzyme Assay. Assays consisted of 50 mM NaOAc pH 5.2, 0.2% Tween 20, 2 mM o-phenylenediamine, 30 mM potassium oxalate, and enzyme in a volume of 100 μL. Turnover was initiated by addition of substrate. Mixtures were incubated at ambient temperature (21–22° C.), and then the reaction was quenched by addition of 10 μL 1 N NaOH. The amount of formate produced in the enzyme-catalyzed reaction was measured using a formate dehydrogenase (FDH) assay consisting of 100 mM potassium phosphate pH 7.8, 1.5 mM NAD+, and 0.1 I.U. FDH (1 mL final volume). Absorbance at 340 nm was measured after incubation at 37° C. for 30 minutes. Formate was quantitated by comparison to a standard curve generated by spiking protein-free OxDC assays with known amounts of sodium formate.

Metal Analysis of *Aspergillus niger* OxDC. Purified *Aspergillus niger* OXDC was treated to remove adventitious, surface-bound metals by incubating 9 mg/mL OxDC (100 μL) with 10 mM o-phenanthroline (10 μL) on ice for 30 minutes. The enzyme was then desalted over G25 Sephadex resin that had been pre-treated with 20 mM NaOAc, pH 5.2, containing 2 mM EDTA and then equilibrated with Chelex-100-treated 20 mM NaOAc buffer, pH 5.2. In these experiments, all glassware was washed with 1 M $HNO_3$ and rinsed with deionized water (18.3 M) to remove exchangeable metal ions prior to use. Samples of OxDC treated in this manner were then divided into two aliquots for EPR and inductively coupled plasma-atomic emission (ICP-AE) spectroscopy. Metal content was determined by ICP-AE spectroscopy using protein samples made by diluting 100 μL of OxDC (0.5 mg) with 9.9 mL deionized water. All analyses were performed in the Department of Chemistry at the University of Florida. Calculations of the metal content in native *Aspergillus niger* OxDC employed standard procedures (see supplementary material).

Chromosomal DNA Cloning. Freeze-dried mycelium (0.5 g) taken from shake cultures of confluent *Aspergillus niger* was gently ground in liquid $N_2$, using a mortar and pestle, to give a fine powder. Care was taken during this procedure so as to prevent shearing high-molecular weight DNA by excessive grinding. The resulting powder was extracted with Qiagen "QBT" buffer (20 mL) supplemented with 0.5% v/v Triton X-100, before the addition of solutions of ribonuclease A (100 μL) and 14 mg/mL Proteinase K (100 μL). The extract was incubated for 30 min at ambient temperature, and then for 15 min at 50° C. before being loaded onto a Qiagen Genomic Tip and purified. The resulting high molecular weight DNA was digested thoroughly using BamHI, EcoRI, HindIII, and PstI restriction enzymes.

Polymerase chain reaction (PCR) primers were designed assuming a close nucleotide sequence relationship between the genes encoding OxDC in *Aspergillus phoenices* (Scelonge et al., 1998) and *Aspergillus niger*. A mutagenic 5'-primer (5'-GTCCTCGAGAAAAGATACCAG-3') (SEQ ID NO. 5) was employed to introduce a XhoI site and a proteolytic cleavage site, for use in future expression experiments, immediately upstream of the codon of Tyr-24 in the putative *Aspergillus niger* gene sequence. This primer was combined with a reverse primer (5'-TCATCTACTCACTTGGGCTCCGAATTG-3') (SEQ ID NO. 6) matching the 3'-end of the gene in *Aspergillus phoenices*. Thirty cycles of amplification were performed (95° C., 1' denaturation; 45° C. primer annealing, 30 s; 74° C. primer extension, 3') with Pfu polymerase (Promega, Madison, Wis.), and the resulting PCR product purified by phenol:chloroform:isoamyl alcohol extraction, chloroform extraction, and ethanol precipitation. The plasmid pPIC9K was digested with SnaBI, treated with alkaline phosphatase, and purified prior to overnight ligation with the purified PCR product. Competent JM109 cells (>$10^8$ CFU/μg) were transformed, and white colonies screened by XhoI digestion of alkaline lysis/miniprepped plasmid DNA. Plasmid that produced two bands upon XhoI digestion was purified, and submitted for nucleotide sequencing at the Interdisciplinary Center for Biotechnology Research (ICBR) at the University of Florida.

Following are examples that illustrate procedures for practicing the invention. These examples should not be construed as limiting. All percentages are by weight and all solvent mixture proportions are by volume unless otherwise noted.

EXAMPLE 1

Isolation, Purification, and Assay of Native Oxalate Decarboxylase from *Aspergillus niger*

Previous studies had shown that the presence of OxDC in the mycelium of *Aspergillus niger* was inversely related to detectable oxalate in the extracellular milieu (Emiliani et al., 1964). This might be rationalized by assuming that there is leakage of protonated oxalic acid back into the fungus when the pH of the culture drops due to excretion of oxalic and citric acids during the early stages of *Aspergillus* growth. As a consequence, OxDC expression is induced so as to reduce oxalate concentrations in the mycelium to a non-toxic level. In light of this hypothesis, literature protocols for inducing OxDC production in *Aspergillus niger* were modified by adding 10 mM sodium oxalate to the minimal media upon which the fungus was grown. Under these conditions, adequate amounts of enzyme could be isolated from the fungal mycelium for the work described here. Previous studies had demonstrated that native *Aspergillus niger* OXDC exhibited notable stability in organic solvents, and so initial purification steps involved precipitation of the enzyme with methanol. Subsequent chromatography using anion exchange and hydrophobic interaction columns gave OxDC as a single band on SDS-PAGE (FIG. 1), with a molecular weight in the range expected based on studies of the enzyme isolated from *Flammulina velutipes* (Kathiara et al., 2000). Purified *Aspergillus niger* OxDC exhibited a specific activity of 10 I.U./mg, as determined from steady-state formate production under initial velocity conditions.

EXAMPLE 2

Deduced Primary Structure of *Aspergillus niger* OxDC

Cloning of both the chromosomal and cDNA copies of the OxDC gene showed that (i) there are only two intron sequences in the *Aspergillus niger* decarboxylase gene (FIG. 3A–3C), in contrast to the 17 reported for the cognate gene in *Flammulina velutipes* (Kesarwani et al., 2000), and (ii) the intron sequences in the gene encoding OxDC in *Aspergillus niger* have canonical 5' and 3' borders (GT-AG) in contrast to those reported to be present in the cognate gene in *Aspergillus phoenices* (Scelonge et al., 1998). The protein product encoded by the yvrk gene in *Bacillus subtilis* (Kunst et al., 1997) shows some homology to *Aspergillus niger* OxDC with 197 (52%) residues in the bacterial OxDC being identical to those in the fungal enzyme.

More importantly for the catalytic mechanism of oxalate degradation, there are two "His-TrpHis" motifs that are conserved among the bacterial and fungal oxalate decarboxylases. Recent work on recombinant *Bacillus subtilis* OXDC suggests that this enzyme contains Mn(II) in its resting state (Tanner et al., 2001; Anand et al., 2002) consistent with our observations on the native *Aspergillus niger* OxDC. In addition, a similar "His-Ile-His" motif present in oxalate oxidase has been shown to be a manganese-binding site by X-ray crystallography (Woo et al., 2000), suggesting a role for at least one, and possibly two metal ions, in OxDC catalysis (Gane et al., 1998).

EXAMPLE 3

Biochemical Characterization of Native *Aspergillus niger* OxDC.

With the successful development of culture conditions and purification procedures to obtain milligram amounts of native *Aspergillus niger* OxDC, the biochemical and spectroscopic properties of the enzyme were investigated. N-terminal sequencing of the purified protein, carried out at the Protein Core Facility of the Interdisciplinary Center for Biotechnology Research (ICBR) at the University of Florida (UF), revealed that phenylalanine is the first residue in the mature enzyme, the initial N-terminal sequence being Phe-Gln-Asp-Lys-Pro-Phe-Thr-Pro-Asp-His-Arg (SEQ ID NO. 7), matching the primary structure deduced from the cloned genes encoding OxDC in both *Aspergillus niger* (vide infra) and *Aspergillus phoenices* (Scelonge et al., 1998) and confirming the identity of the isolated protein. It was anticipated that the N-terminal region would be Tyr-Gln-Gln-Asp (SEQ ID NO. 8) on the basis of the primary structure deduced from the cloned gene, and shows that the fungal enzyme is synthesized with a leader peptide that may be important in cellular trafficking (Walter et al., 1994). MALDI-TOF measurements on the purified fungal OxDC indicated that the mass of a single subunit of the enzyme is 48,700–48,800 Da, which is consistent with that calculated for the deduced amino acid sequence with the observed N-terminal residue, assuming that the protein contains metal ions and is glycosylated. While the bacterial OxDC has been shown to exist as a hexamer consisting of a hypothetical dimer of trimers (Tanner et al., 2001), the quaternary structure of the fungal enzyme remains to be unambiguously established.

Despite a failure to detect metal-dependence of turnover in earlier studies of native *Aspergillus niger* OxDC (Emiliani et al., 1968), extensive comparisons of the deduced primary structures for oxalate oxidases and oxalate decarboxylases from a variety of sources suggest that OxDC contains two metal-binding sites per polypeptide. ICP-AE analysis of the purified enzyme from *Aspergillus niger* showed the sample to contain approximately 0.75 and 0.25 subunit-equivalents Mn and Cu, respectively. If bound Cu and Mn ions were both required for catalysis, it is anticipated that the maximum activity of the purified fungal enzyme would correspond to $3/16$ of the theoretical $V_{max}$. While this is approximately the activity observed in the *Aspergillus niger* OxDC purified using the protocols described herein relative to that reported in previous studies of this enzyme (Emiliani et al., 1968), the role of Cu in catalytic activity appears uncertain given that the recombinant bacterial OxDC has been demonstrated to contain only Mn (Tanner et al., 2001). In any case, the metal content of the purified fungal OxDC is consistent with occupancy of no more than 50% of the potential active sites by either Cu or Mn.

EXAMPLE 4

Cloning, Expression and Purification of *Bacillus subtilis* Oxalate Decarboxylase Since the Yvrk-encoded protein had no known function at the time we initiated these studies, the upstream and downstream PCR primers were designed based on the published sequence of the gene in the GenBank database, in order to clone the bacterial gene, and express and characterize its encoded protein. These primers were such that the yvrK coding sequence would be in-frame with the T7 control elements that are part of the pET-9a expression vector (Stratagene). An NdeI site was included at the N-terminal methionine, and a BamHI site after the termination codon of yvrK. *B. subtilis* 168 genomic DNA was purified from an overnight 5 mL culture using a Genomic DNA Miniprep kit (Qiagen). The yvrK sequence was amplified for 31 cycles (95° C. denaturation, 30s; 45° C. annealing, 30 s; 74° C. extension, 2 min). The resulting DNA was digested with NdeI and BamHI, then ligated into pET-9a digested similarly. Competent JM109 cells were transformed with the ligation mixture and with pET-9a as a control, and transformants selected on Luria-Bertani broth (LB) containing 30 µg/mL kanamycin (LBK). The resulting colonies were screened by NdeI-BamHI digestion to confirm the presence of a ~1153 bp insert, and the sequence of the cloned gene was checked by sequencing. A plasmid produced from pET-9a/yvrK:JM109 by standard alkaline lysis miniprep was used to transform the expression strain BL21(DE3), and the expression of the Yvrk-encoded protein was tested by inoculating 0.5 L of LBK supplemented with pET-9a/yvrK:BL21(DE3). The cells were grown at 37° C. and shaken at 200 r.p.m. When the cultures reached $A_{600}$ of 2 they were heat shocked in water bath at 42° C. for 18 min before the addition of isopropyl thiogalactoside (IPTG) and MnCl$_2$ to final concentrations 1 and 5 mM respectively. The cells were harvested after 4 h of shaking by centrifugation (5,000×g, 15 min, 4° C.). Pellets were resuspended in 50 mL lysis buffer (50 mM Tris/HCl pH 7; 10 μM MnCl$_2$) and sonicated for 30 s at 80% power. After sonication, lysis pellets were separated from the crude extract by centrifugation (8000 rpm, 20 min, 4° C.) and resuspended in 50 mL of extraction buffer containing 1 M sodium chloride, 0.1% Triton X-100, and 10 mM 2-mercaptoethanol. The mixture was stirred overnight at room temperature. Cell debris was removed by centrifugation and the supernatant was combined with the crude extract. This solution (100 mL) was diluted 10-fold before it was applied to a 2.5×30 cm DEAE-Sepharose Fast Flow (Sigma) column. This column was washed with 100 mL imidazole HCl buffer (20 mM; pH 7.0 and 10 μM MnCl$_2$) and developed with a 500 mL M NaCl gradient (0 to 1M gradient). Ten mL fractions were collected and assayed for their ability to oxidize o-phenylenediamine, which is a side-reaction catalyzed by OxDC. Fractions exhibiting activity were pooled and solid (NH$_4$)$_2$SO$_4$ was added to a 70% saturation. The precipitate was removed by centrifugation (8,000×g, 30 min, 4° C.) and redissolved in 200 ml imidazole.HCl buffer and the supernatant was loaded onto a phenyl-Sepharose Hi-Performance (Amersham Pharmacia Biotech) column. The column was washed with imidazole hydrochloride buffer (50 mM, pH 7.0, containing 10 μM MnCl$_2$) and developed with a 500 mL (NH$_4$)$_2$SO$_4$ gradient (1.7 to 0 M). The fractions were pooled as for the DEAE column and diluted 15-fold before they were loaded onto a Q-Sepharose Hi-Performance (Amersham Pharmacia Biotech) column. The protein was eluted with an imidazole hydrochloride buffer (50 mM, pH 7.0, containing 10 μM MnCl$_2$) and a 500 mL NaCl gradient (0 to 1 M) as for the DEAE column. Protein precipitated with 70% ammonium sulfate was centrifuged and redissolved in 10 ml 20 mM hexamethylenetetramine.HCl pH 7. Ammonium sulfate was dialyzed out against 1 L of the same amine buffer for 5 h at 4° C. Protein solution was concentrated by centrifugal concentrator to final volume ~1 ml. Aliquots were flash-frozen in liquid nitrogen and stored at −80° C. This procedure gave highly purified OxDC in yields of up to 30–40 mg/L with a specific activity of approximately 50 IU/mg.

It should be understood that the examples and embodiments described herein are for illustrative purposes only and that various modifications or changes in light thereof will be suggested to persons skilled in the art and are to be included within the spirit and purview of this application.

REFERENCES

WO 98/52586

U.S. Pat. No. 6,355,242

Allison, M. J., H. M. Cook (1981) "Oxalate degradation by microbes of the large bowel of herbivores: the effect of dietary oxalate" *Science* 212:675–676.

Allison, M. J., K. A. Dawson, W. R. Mayberry, J. G. Foss (1985) "*Oxalabacter formigenes* gen. nov., sp. nov.: oxalate-degrading anaerobes that inhabit the gastrointestinal tract" Arch. *Microbiol.* 141:1–7.

Allison, M. J., H. M. Cook, D. B. Milne, S. Gallagher, R. V. Clayman (1986) "Oxalate degradation by gastrointestinal bacteria from humans" *J. Nutr.* 116:455–460.

Allison, M J., S. L. Daniel, N. A. Cornick (1995) "Oxalate-degrading bacteria" In Khan, S. R. (ed.), Calcium Oxalate in Biological Systems CRC Press.

Altschul et al. (1990) *J. Mol. Biol.* 215:402–410.

Altschul et al. (1997) *Nucl. Acids Res.* 25:3389–3402.

Anand, R., Dorrestein, P. C., Kinsland, C., Begley, T. P., and Ealick, S. E. (2002) *Biochemistry* 41:7659–7669.

Baldwin, J., Krebs, C., Ley, B. A., Edmondson, D. E., Huynh, B. H., and Bollinger, J. M. J. (2000) *J. Am. Chem. Soc.* 122:12195–12206.

Bar, G., Bennati, M., Nguyen, H.-H. T., Ge, J., Stubbe, J., and Griffin, R. G. (2001) *J. Am. Chem. Soc.* 123:3569–3576.

Bard, A. J., and Lund, H. (1978) in *Encyclopedia of Electrochemistry of the Elements* pp 267–328, Marcel Dekker, Inc., New York.

Basosi, R., Antholine, W. E., and Hyde, J. S. (1993) in *EMR of Paramagnetic Molecules* (Berliner, L. J., and Reuben, J., Eds.) pp 103–50, Plenum Press, New York.

Beltz, G. A., K. A. Jacobs, T. H. Eickbush, P. T. Cherbas, and F. C. Kafatos (1983) *Methods of Enzymology*, R. Wu, L. Grossman and K. Moldave [eds.] Academic Press, New York 100:266–285.

Daniel, S. L., P. A. Hartman, M. J. Allison (1987) "Microbial degradation of oxalate in the gastrointestinal tracts of rats" *Appl. Environ. Microbiol.* 53:1793–1797.

Dawson, K. A., M. J. Allison, P. A. Hartman (1980) "Isolation arid some characteristics of anaerobic oxalate-degrading bacteria the rumen" *Appl. Environ. Microbiol.* 40:833–839.

Doane, L. T., M. Liebman, D. R. Caldwell (1989) "Microbial oxalate degradation: effects on oxalate and calcium balance in humans" *Nutrition Research* 9:957–964.

Drummond, A. Y., and Waters, W. A. (1953) *J. Chem. Soc.,* 435–443.

Dunwell, J. M., Khuri, S., and Gane, P. J. (2000) *Microbiol. Mol. Biol. Rev.* 64:153–179.

Dutton, M. V., and Evans, C. S. (1996) *Can. J. Microbiol.* 42:881–895.

Edlund, O., Lund, A., and Graslund, A. (1973) *J. Magn. Reson.* 10:7–14.

Emiliani, E., and Bekes, P. (1964) *Arch. Biochem. Biophys.* 105:488–493.

Emiliani, E., and Riera, B. (1968) "Enzymatic Oxalate Decarboxylation in *Aspergillus niger*. II. Hydrogen Peroxide Formation and Other Characteristics of the Oxalate Decarboxylase" *Biochem. Biophys. Acta* 167:414–421.

Gane, P. J., Dunwell, J. M., and Warwicker, J. (1998) "Modeling Based on the Structure of Vicilins Predicts a Histidine Cluster in the Active Site of Oxalate Oxidase" *J. Mol. Evol.* 46:488–493.

Halcrow, M. A. (2001) "Chemically modified amino acids in copper proteins that bind or activate dioxygen" *Angew. Chem., Int. Ed. Engl.* 40:346–349.

Halliwell, B. (1972) "Non-Enzymic Catalysis of Oxalate Decarboxylation by Light and Flavins" *Biochem. J.* 129:497–498.

Hodgkinson, A. (1977) *Oxalic Acid in Biology and Medicine*, Academic Press, New York.

Karlin and Altschul (1990) *Proc. Natl. Acad. Sci. USA* 87:2264–2268.

Karlin and Altschul (1993) *Proc. Natl. Acad. Sci. USA* 90:5873–5877.

Kathiara, M., Wood, D. A., and Evans, C. S. (2000) "Estimating Relative Decline in Populations of Subterranean (Isoptera: Rhinotermitidae) Due to Baiting" *Mycol. Res.* 104:345–350.

Kesarwani, M., Azarn, M., Natarajan, K., Mehta, A., and Datta, A. (2000) "Oxalate Decarboxylase from Collybia Velutipes. Molecular Cloning and its Overexpression to Confer Resistance to Fungal Infection in Transgenic Tobacco and Tomato" *J. Biol. Chem.* 275:7230–7238.

Kimmerling, E. A., Fedrick, J. A., and Tenholder, M. F. (1992) "Invasive *Aspergillus niger* with Fatal Pulmonary Oxalosis in Chronic Obstructive Pulmonary Disease" *Chest* 101:870–872.

Kotsira, V. P., and Clonis, Y. D. (1997) "Oxalate Oxidase from Barley Roots: Purification to Homogeneity and Study of Some Molecular, Catalytic, and Binding Properties" *Arch. Biochem. Biophys.* 340:239–249.

Krebs, C., Chen, S., Baldwin, J., Ley, B. A., Patel, U., Edmondson, D. E., Huynh, B. H., and Bollinger, J. M. J. (2000) *J. Am. Chem. Soc.* 122:12207–12219.

Kunst, F. et al. (1997) "The Complete Genome Sequence of the Gram-Positive Bacterium *Bacillus Subtilis*" *Nature* 390:249–256.

Landry, M. L. M., and Parkins, C. W. (1993) "Calcium Oxalate Crystal Deposition in Necrotizing Otomycosis Caused by *Aspergillus niger*" *Mod. Pathol.* 6:493–496.

Lillehoj, E. B., and Smith, F. G. (1965) *Arch. Biochem. Biophys.* 109:216–220.

Mehta, A., and Datta, A. (1991) "Oxalate Decarboxylase from Collybia Velutipes. Purification, Characterization, and cDNA Cloning" *J. Biol. Chem.* 266:23548–23553.

Metzger, J. B., Garagusi, V. F., and Kerwin, D. M. (1984) "Pulmonary Oxalosis Caused by *Aspergillus niger*" *Am. Rev. Respir. Dis.* 129:501–502.

Neves-Petersen, M. T., Petersen, E. I., Fojan, P., Noronha, M., Madsen, R. G., Petersen, S. B. (2001) "Engineering the pH-optimum of a triglyceride lipase: from predictions based on electrostatic computations to experimental results" *Journal of Biotechnology* 87(3):225–254.

Nielsen, J. E., Beier, L., Otzen, D., Borchert, T. V., Frantzen, H. B., Andersen, K. V., Svendsen, A. (1999) "Electrostatics in the active site of an alpha-amylase" *European Journal of Biochemistry* 264(3):816–824.

Padmakumar, R., and Ruma Banerjee. (1995) "Evidence from Electron Paramagnetic Resonance Spectroscopy of the Participation of Radical Intermediates in the Reaction Catalyzed by Methylmalonyl-Coenzyme A Mutase" *J. Biol. Chem.* 270:9295–9300.

Parast, C. V., Wong, K. K., Lewisch, S. A., Kozarich, J. W., Peisach, J., and Magliozzo, R. S. (1995) *Biochemistry* 34:2393–2399.

Parast, C. V., Wong, K. K., and Kozarich, J. W. (1995a) "Hydrogen Exchange of the Glycyl Radical of Pyruvate Formate-lyase is Catalyzed by Cysteine 419" *Biochemistry* 34:5712–5717.

Persson, A. L., Sahlin, M., and Sjöberg, B.-M. (1998) "Cysteinyl and Substrate Radical Formation in Active Site Mutant E411Q of *Escherichia coli* Class I Rib nucleotide Reductase" *J. Biol. Chem.* 273:31016–31020.

Quayle, J. R. (1963) *Biochem. J.* 89:492–503.

Requena, L., and Bornemann, S. (1999) "Barley (*Hordeum vulgare*) Oxalate Oxidase is a Manganese-Containing Enzyme" *Biochem. J.* 343:185–190.

Rupp, H., Cammack, R., Rao, K. K., and Hall, D. O. (1978) "Electron Spin Relaxation of Iron-Sulphur Proteins Studied by Microwave Power Saturation" *Biochim. Biophys. Acta* 537:255–269.

Maniatis, T., E. F. Fritsch, J. Sambrook (1982) *Molecular Cloning: A Laboratory Manual*, Cold Spring Harbor Laboratory, Cold Spring Harbor, N.Y.

Scelonge, C. J., and Bidney, D. L. (1998) in *PCT Intl. Patent* 06297425, Pioneer Hi-Bred International, Inc., USA.

Seebach, D. (1979) *Angew. Chem. Intl. Ed. Engl.* 18:239–258.

Shaw, A., Bott, R., Day, A. G. (1999) "Protein engineering of alpha-amylase for low pH performance" *Current Opinion in Biotechnology* 10(4):349–352.

Shimazono, H. (1955) *J. Biochem.* (Tokyo) 42:321–340.

Shimazono, H., and Hayaishi, O. (1957) *J. Biol. Chem.* 227:151–159.

Solomons, C. C., M. H. Melmed, S. M. Heitler (1991) "Calcium citrate for vulvar vestibulitis" *Journal of Reproductive Medicine* 36:879–882.

Su, Q. J., and Klinman, J. P. (1998) "Probing the Mechanism of Proton Coupled Electron Transfer to Dioxygen: The Oxidative Half-Reaction of Bovine Serum Amine Oxidase" *Biochemistry* 37:12513–12525.

Tanner, A., and Bornemann, S. (2000) "*Bacillus Subtilis* YvrK is an Acid-induced Oxalate Decarboxylase" *J. Bacteriol.* 182:5271–5273.

Tanner, A., Bowater, L., Fairhurst, S. A., and Bornemann, S. (2001) "Oxalate Decarboxylase Requires Manganese and Dioxygen for Activity. Overexpression and Characterization of *Bacillus subtilis* YvrK & YoaN" *J. Biol. Chem.* 276:14627–14634.

Villafranca, J. J., Ash, D. E., and Wedler, F. C. (1976) *Biochemistry* 15:544–553.

Walter, P., and Johnson, A. E. (1994) "Signal Sequence Recognition and Protein Targeting to the Endoplasmic Reticulum Membrane" *Annu. Rev. Cell. Biol.* 10:87–119.

Weil, J. A., Bolton, J. R., and Wertz, J. E. (1994) *Electron Paramagnetic Resonance: Elementary Theory and Practical Applications*, John Wiley & Sons, Inc., New York.

Woo, E. J., Dunwell, J. M., Goodenough, P. W., Marvier, A. C., and Pickersgill, R. W. (2000) "Germin is a Manganese Containing Homohexamer with Oxalate Oxidase and Superoxide Dismutase Activities" *Nature Struct. Biol.* 7:1036–1040.

We claim:

1. An isolated polynucleotide encoding an oxalate decarboxylase enzyme of *Aspergillus*, wherein said polynucleotide encodes an oxalate decarboxylase enzyme comprising the amino acid sequence shown in SEQ ID NO. 4, or an enzymatically active fragment thereof.

2. An isolated polynucleotide encoding an oxalate decarboxylase enzyme of *Aspergillus*, wherein said polynucleotide encodes an oxalate decarboxylase enzyme comprising the amino acid sequence shown in SEQ ID NO. 3, or an enzymatically active fragment thereof.

3. The isolated polynucleotide according to claim 2, wherein said polynucleotide comprises the nucleotide sequence shown in SEQ ID NO. 2, or a fragment thereof encoding an enzymatically active oxalate decarboxylase.

4. The isolated polynucleotide according to claim 2, wherein said polynucleotide comprises the nucleotide sequence shown in SEQ ID NO. 1, or a fragment thereof encoding an enzymatically active oxalate decarboxylase.

5. An isolated cell, or progeny thereof, transformed with a polynucleotide of claim 1.

6. The isolated cell according to claim 5, wherein said cell is a bacterial cell, animal cell, or plant cell.

7. The isolated cell according to claim 5, wherein said cell is lyophilized or frozen.

8. An isolated cell, or progeny thereof, transformed with a polynucleotide of claim 2.

9. The isolated cell according to claim 8, wherein said cell is a bacterial cell, animal cell, or plant cell.

10. The isolated cell according to claim 8, wherein said cell is lyophilized or frozen.

* * * * *

UNITED STATES PATENT AND TRADEMARK OFFICE
CERTIFICATE OF CORRECTION

PATENT NO.    : 6,929,940 B1
DATED         : August 16, 2005
INVENTOR(S)   : Richards et al.

It is certified that error appears in the above-identified patent and that said Letters Patent is hereby corrected as shown below:

Column 2,
Line 50, "of OXDC" should read -- of OxDC --.
Scheme 1 (A),

" $\xrightarrow{\quad}$ —CO$_2$ " should read -- $\xrightarrow{\quad}$ -CO$_2$ -- and " $\xrightarrow{\quad}$ —HCO$_2^-$ " should read -- $\xrightarrow{\quad}$ -HCO$_2^-$ --.

Column 3,
Scheme 1 (B)

" $\xrightarrow{\quad}$ —CO$_2$ " should read -- $\xrightarrow{\quad}$ -CO$_2$ --, and " $\xrightarrow{H^+}$ —H$_2$O$_2$ " should read -- $\xrightarrow{H^+}$ -H$_2$O$_2$ --.

Scheme 1 (legend), "and formulate via" should read -- and formate via --; and "manganese ion (Mn+)" should read -- manganese ion ($M^{n+}$) --.

Column 6,
Line 4, "also showing bold" should read -- also shown in bold --.
Line 11, "*subtilus*" should read -- *subtilis* --.

Column 10,
Line 53, "for OXDC" should read -- for OxDC --.
Line 66, "Native OXDC" should read -- Native OxDC --.

Column 11,
Line 53, "*Aspergillus niger* OXDC was" should read -- *Aspergillus niger* OxDC was --.

UNITED STATES PATENT AND TRADEMARK OFFICE
CERTIFICATE OF CORRECTION

PATENT NO. : 6,929,940 B1
DATED : August 16, 2005
INVENTOR(S) : Richards et al.

It is certified that error appears in the above-identified patent and that said Letters Patent is hereby corrected as shown below:

Column 13,
Line 6, "OXDC exhibited" should read -- OxDC exhibited --.
Line 35, "two "His-TrpHis" motifs" should read -- two "His-Trp-His" motifs --.
Line 38, "OXDC suggests" should read -- OxDC suggests --.

Column 15,
Line 17, "100 mL imidazole HCl buffer" should read -- 100 mL imidazole·HCl buffer --.
Line 24, "200 ml imidazole.HCl buffer" should read -- 200 mL imidazole·HCl buffer --.
Line 38, "hexamethylenetetramine.HCl pH 7." should read
-- hexamethylenetetramine·HCl pH 7. --.

Column 16,
Line 23, "arid some" should read -- and some --.
Line 63, "Azarn, M.," should read -- Azam, M. --.

Column 18,
Line 30, "and Bomemann, S." should read -- and Bornemann, S. --.

Signed and Sealed this

Twenty-fourth Day of January, 2006

JON W. DUDAS
*Director of the United States Patent and Trademark Office*